United States Patent
Lee

(10) Patent No.: US 12,246,331 B2
(45) Date of Patent: Mar. 11, 2025

(54) AIR PURIFIER FOR IMPROVING REMOVAL PERFORMANCE OF HAZARDOUS SUBSTANCE AND VIRUS IN AIR

(71) Applicant: AHAINC CO., LTD., Gimpo-si (KR)

(72) Inventor: Chang Min Lee, Namyangju-si (KR)

(73) Assignee: AHAINC CO., LTD., Gimpo-si (KR)

(*) Notice: Subject to any disclaimer, the term of this patent is extended or adjusted under 35 U.S.C. 154(b) by 510 days.

(21) Appl. No.: 17/616,903

(22) PCT Filed: Nov. 12, 2021

(86) PCT No.: PCT/KR2021/016479
§ 371 (c)(1),
(2) Date: Dec. 6, 2021

(87) PCT Pub. No.: WO2022/108247
PCT Pub. Date: May 27, 2022

(65) Prior Publication Data
US 2022/0347696 A1    Nov. 3, 2022

(30) Foreign Application Priority Data

Nov. 17, 2020  (KR) .................. 10-2020-0153516
Dec. 3, 2020   (KR) .................. 10-2020-0167427
Dec. 31, 2020  (KR) .................. 10-2020-0189375

(51) Int. Cl.
*B03C 3/38*    (2006.01)
*B03C 3/51*    (2006.01)
*B03C 3/82*    (2006.01)

(52) U.S. Cl.
CPC ............... *B03C 3/38* (2013.01); *B03C 3/51* (2013.01); *B03C 3/82* (2013.01)

(58) Field of Classification Search
CPC .... B03C 3/08; B03C 3/11; B03C 3/12; B03C 3/19; B03C 3/368; B03C 3/38;
(Continued)

(56) References Cited

U.S. PATENT DOCUMENTS 7,258,715 B2 *  8/2007  Cox ..................... B03C 3/74
                                                       55/494
7,313,342 B2 * 12/2007  Katayama ........... G03G 21/206
                                                       399/93
(Continued)

FOREIGN PATENT DOCUMENTS

EP   1867346 A1 * 12/2007 ............. A61L 9/015
JP   0788399 A     4/1995
(Continued)

OTHER PUBLICATIONS

Translation of the International Preliminary Report on Patentability issued on May 16, 2023 in PCT/KR2021/016479.
(Continued)

*Primary Examiner* — Christopher P Jones
*Assistant Examiner* — Sonji Turner
(74) *Attorney, Agent, or Firm* — Honigman LLP

(57) ABSTRACT

An air purifier capable of removing hazardous substances and viruses from air. The air purifier further includes: a body having an air inlet formed on a lower end thereof, an air outlet formed on an upper end thereof, and a flow path formed therein to move air upward; a pre-filter disposed in the flow path of the body; a box-shaped cell type discharge device disposed in the flow path of the body to generate active species; a dust collection device in the flow path of the body and having a discharge part with a linear discharge electrode and a dust collection part for collecting the dust charged through the discharge part; an ozone removal device in the flow path of the body to remove ozone generated from the discharge device and/or the dust collection device; and an air fan disposed in the flow path of the body.

13 Claims, 24 Drawing Sheets

(58) Field of Classification Search
CPC .... B03C 3/41; B03C 3/49; B03C 3/51; B03C 3/70; B03C 3/78; B03C 3/82; B03C 3/86; B03C 2201/04; B03C 2201/10; B03C 2201/28; A61L 9/22; F24F 3/16; F24F 8/10; F24F 8/192; F24F 13/20
See application file for complete search history.

(56) References Cited

U.S. PATENT DOCUMENTS

| | | | | |
|---|---|---|---|---|
| 8,454,733 | B2* | 6/2013 | Tanaka | B03C 3/383 96/97 |
| 8,454,734 | B2* | 6/2013 | Haruna | B03C 3/155 96/97 |
| 8,889,079 | B2* | 11/2014 | Zahedi | C01B 13/0288 422/171 |
| 9,040,008 | B2* | 5/2015 | Zahedi | B01D 53/323 588/900 |
| 2006/0272505 | A1* | 12/2006 | Tanaka | A61L 9/22 96/96 |
| 2008/0250930 | A1* | 10/2008 | Bologa | B03C 3/16 96/86 |

FOREIGN PATENT DOCUMENTS

| | | | |
|---|---|---|---|
| JP | 3038757 U | | 6/1997 |
| JP | 09285739 A | | 11/1997 |
| JP | 10113577 A | | 5/1998 |
| JP | H1147635 A | * | 2/1999 |
| JP | 2002346334 A | | 12/2002 |
| JP | 2007196199 A | | 8/2007 |
| JP | 2009125122 A | | 6/2009 |
| KR | 20000059884 A | * | 10/2000 |
| KR | 1020050066686 | | 6/2005 |
| KR | 100527209 B1 | * | 11/2005 |
| KR | 1020070028479 | | 3/2007 |
| KR | 1020110090539 | | 8/2011 |
| KR | 1019927430000 | | 6/2019 |
| KR | 1020190084379 | | 7/2019 |

OTHER PUBLICATIONS

International Preliminary Report on Patentability issued on May 16, 2023 in PCT/KR2021/016479.
Translation of the International Search Report issued on Mar. 15, 2022 in PCT/KR2021/016479.
International Search Report issued on Mar. 15, 2022 in PCT/KR2021/016479.
Translation of the Written Opinion of the International Searching Authority issued on Mar. 15, 2022 in PCT/KR2021/016479.
Written Opinion of the International Searching Authority issued on Mar. 15, 2022 in PCT/KR2021/016479.

* cited by examiner

[Fig. 1]
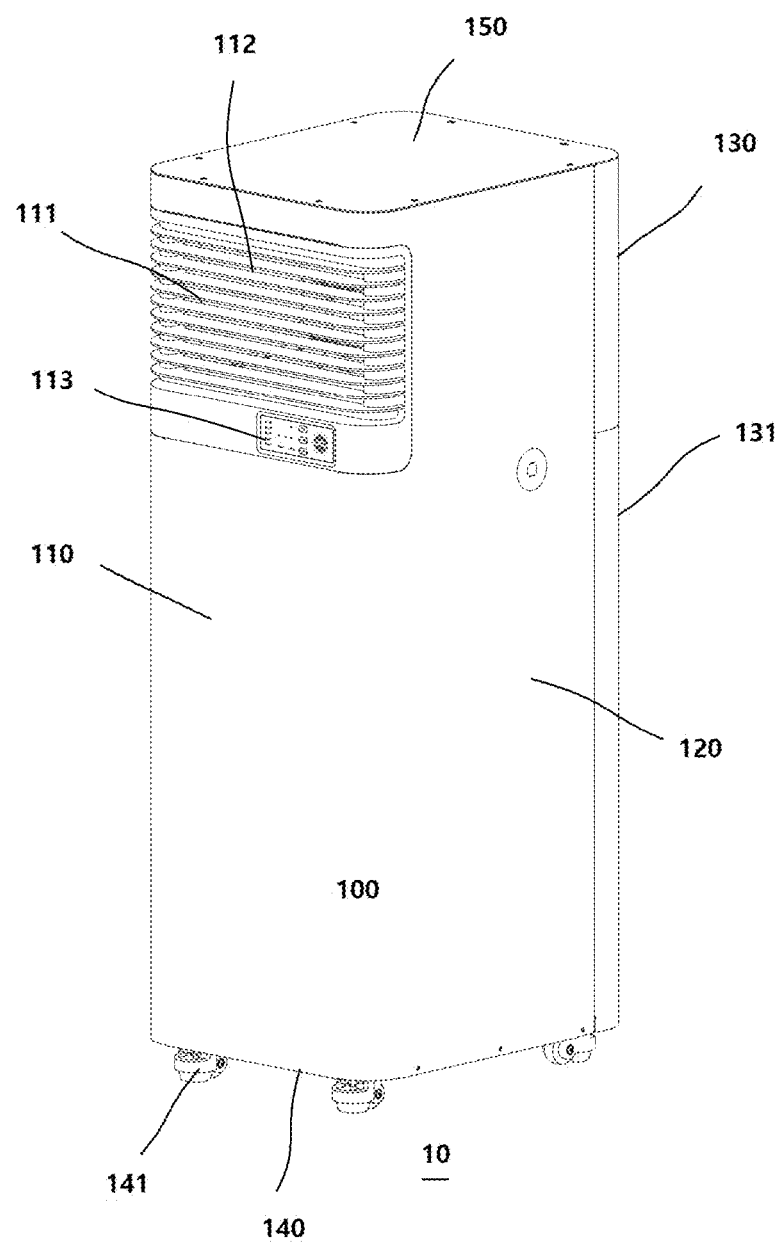

[Fig. 2]
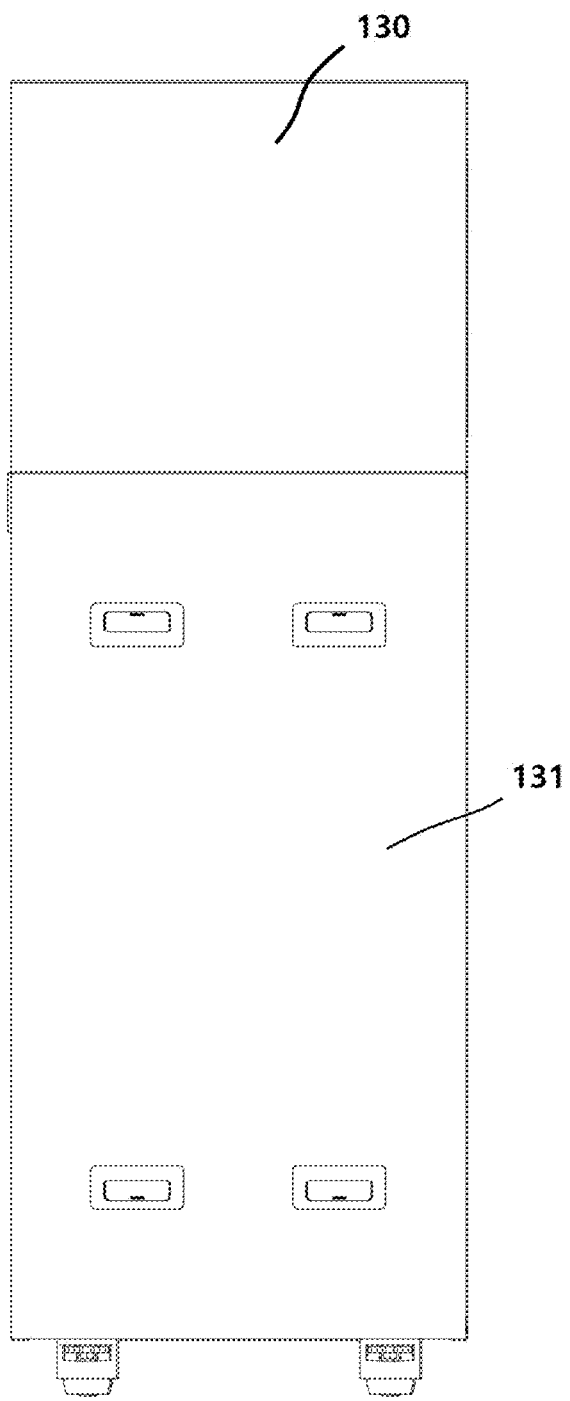

[Fig. 3]
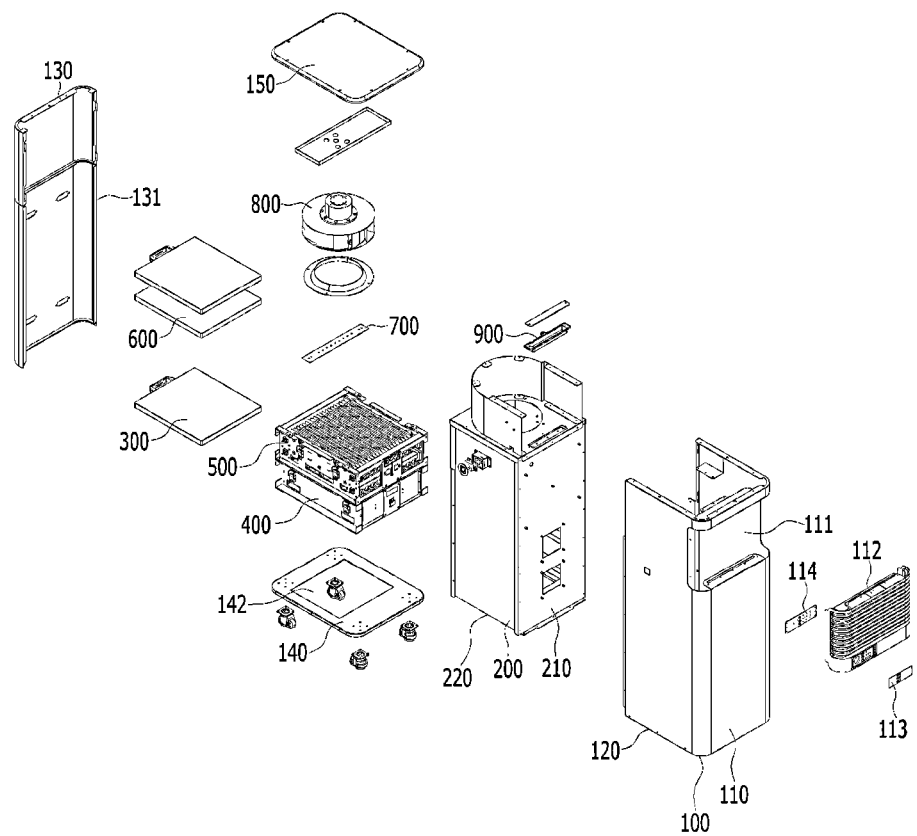

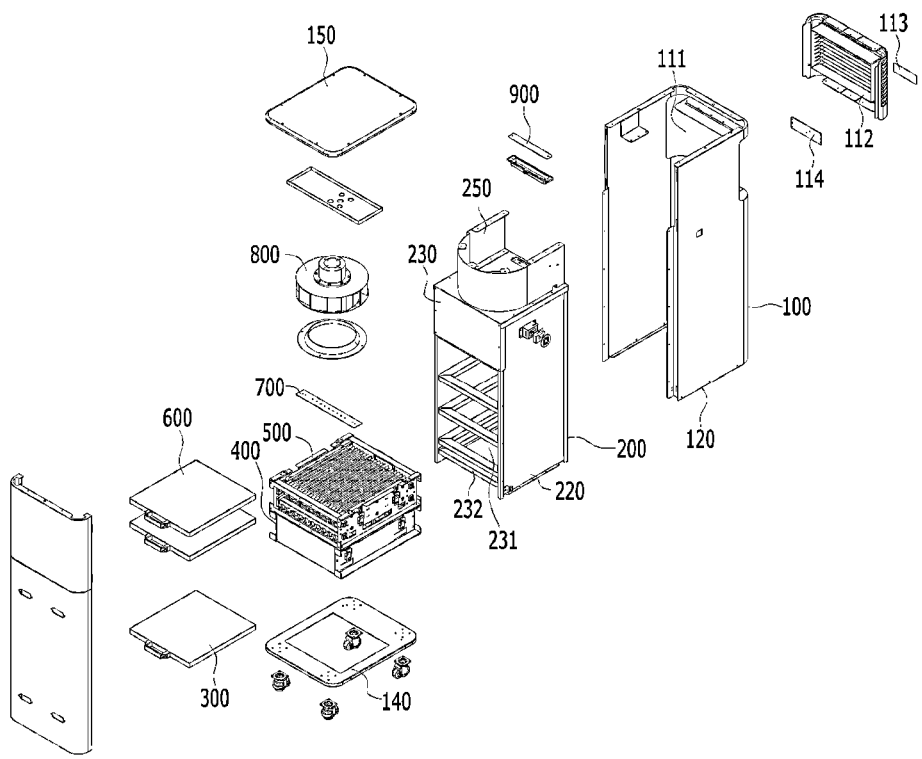
[Fig. 4]

[Fig. 5]
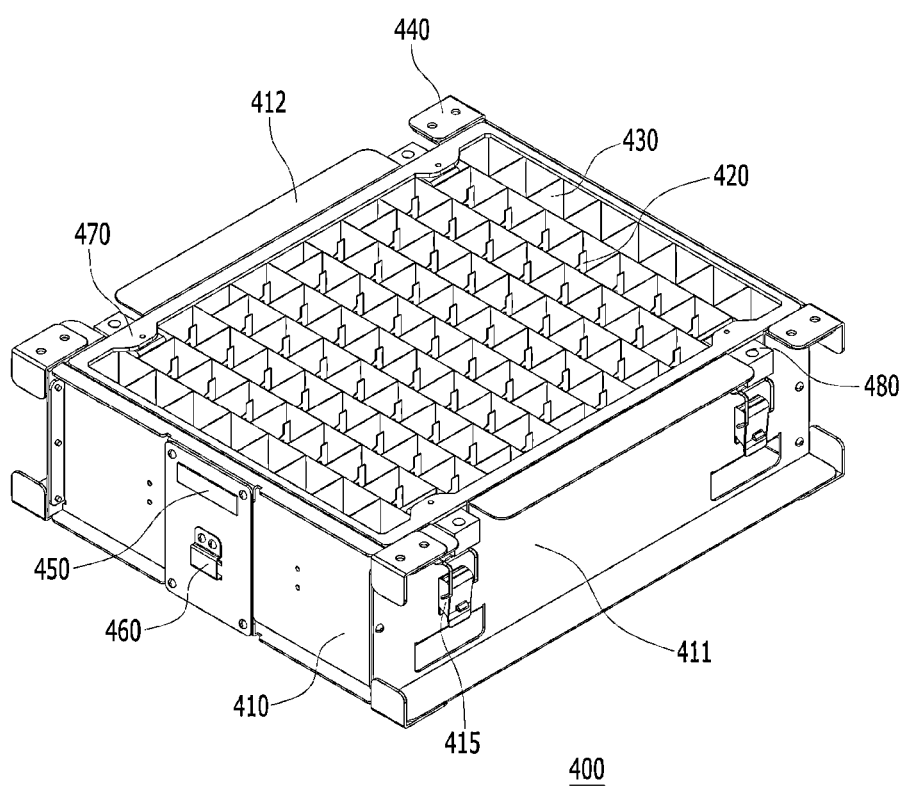

[Fig. 6]
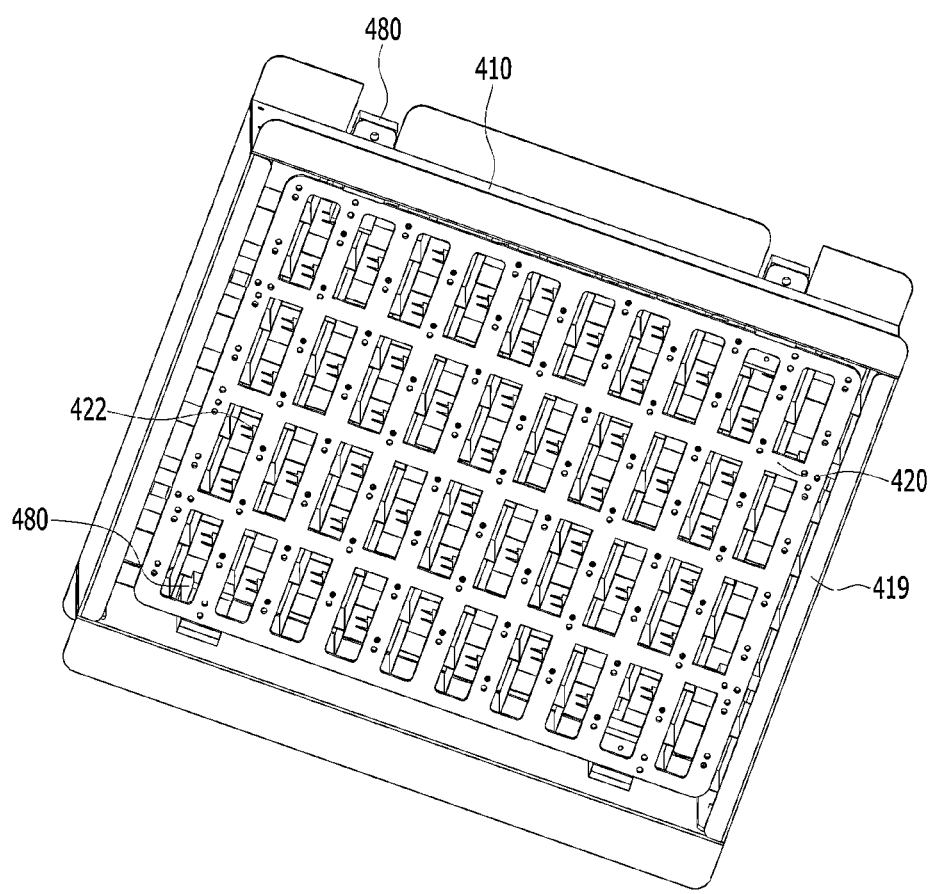

[Fig. 7]
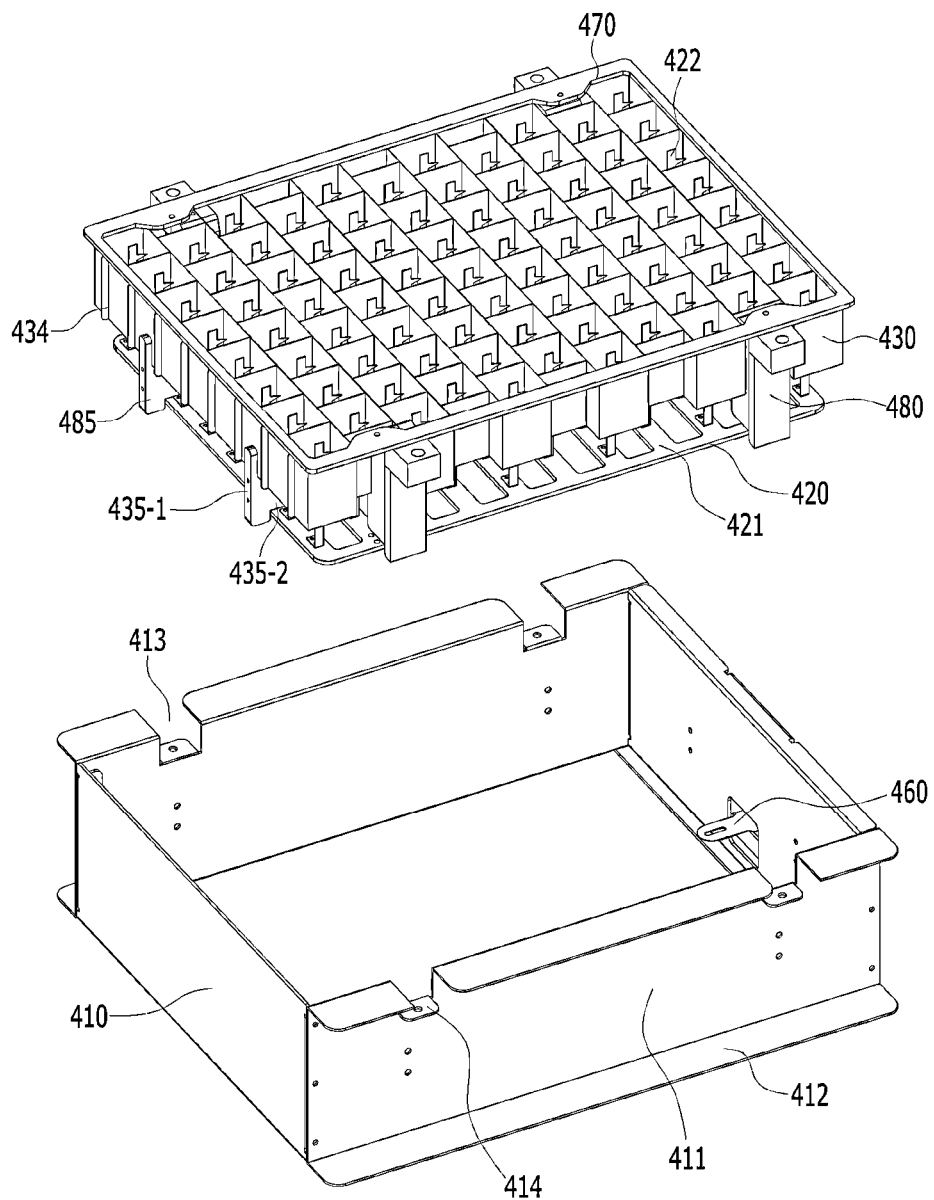

[Fig. 8]
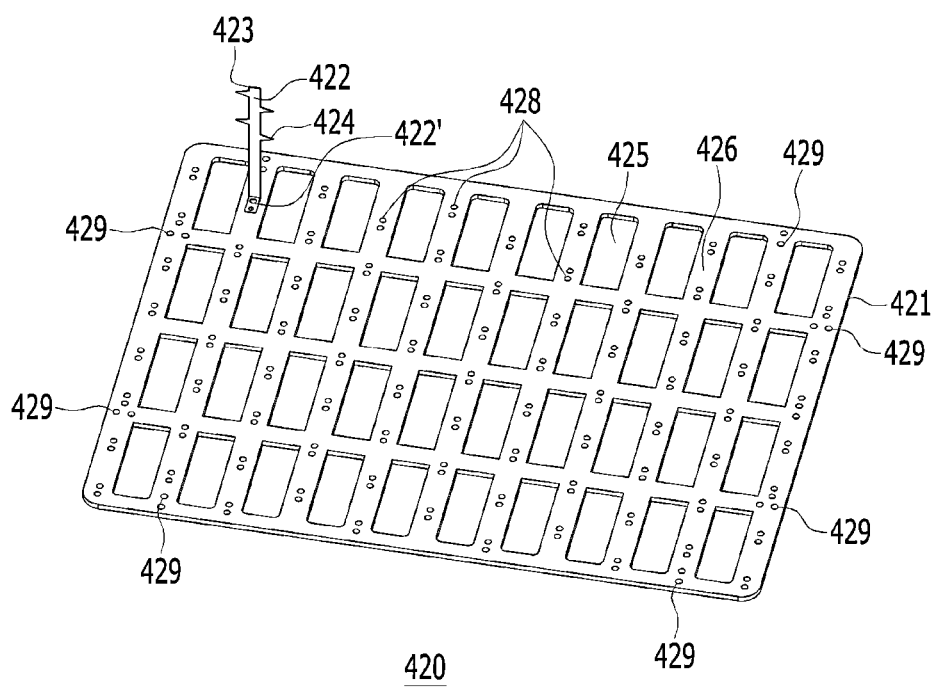

[Fig. 9]
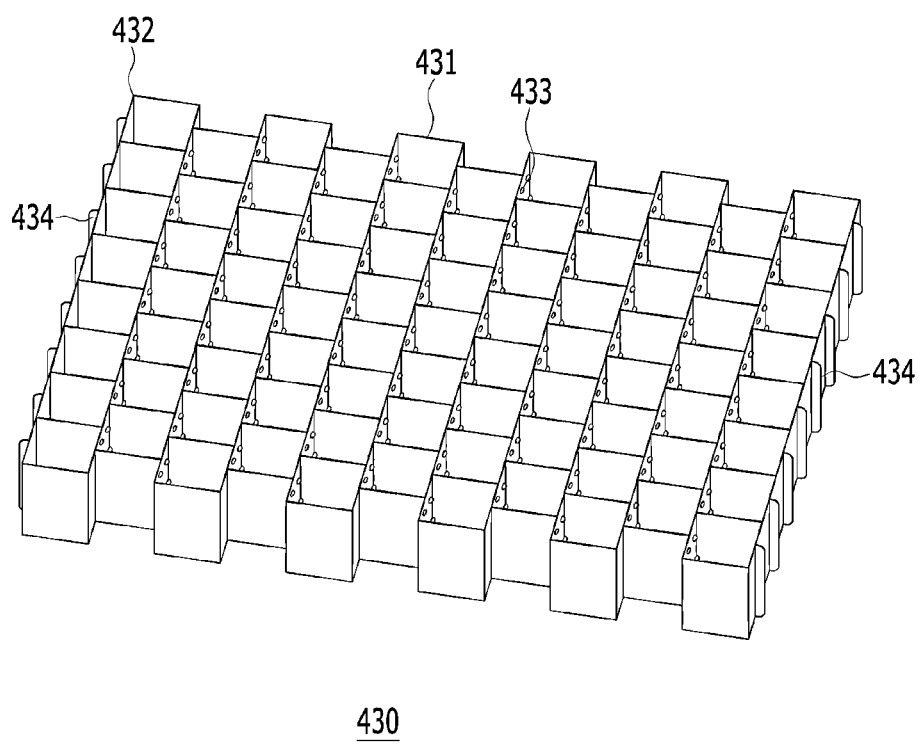

[Fig. 10]
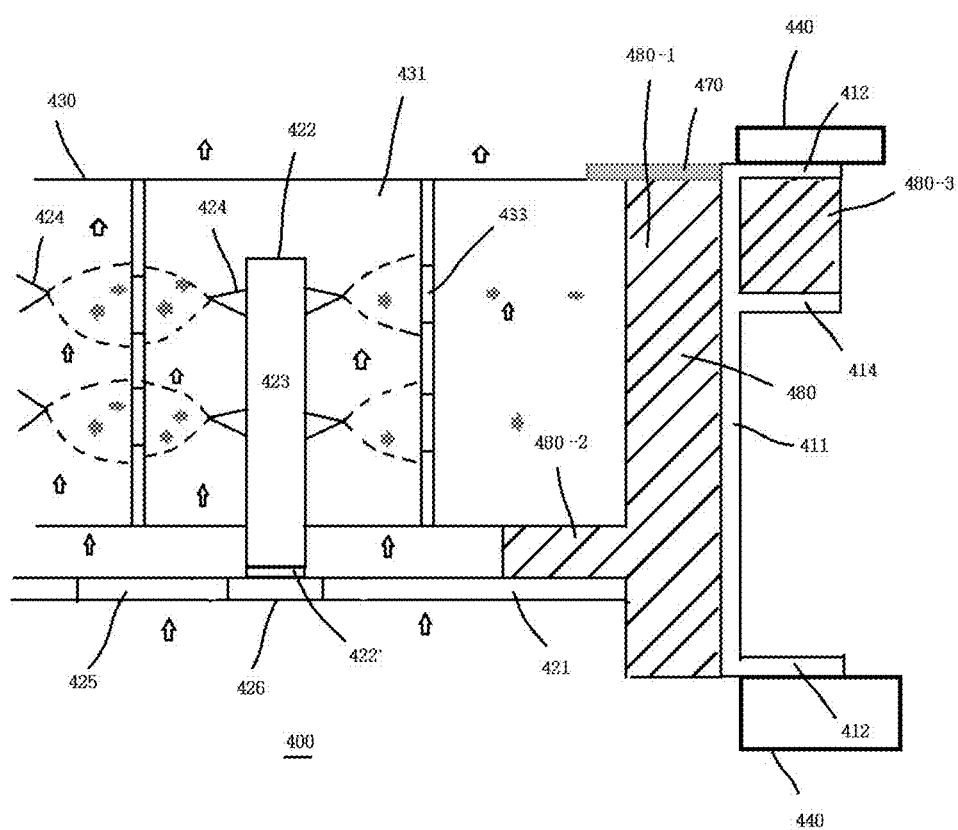

[Fig. 11]
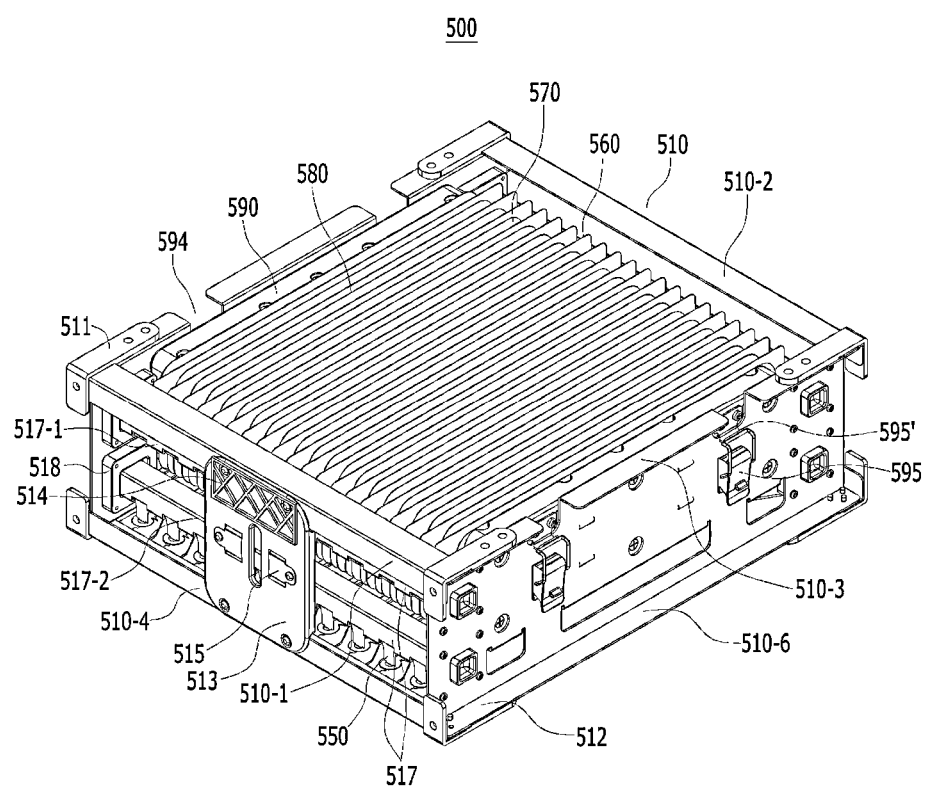

[Fig. 12]
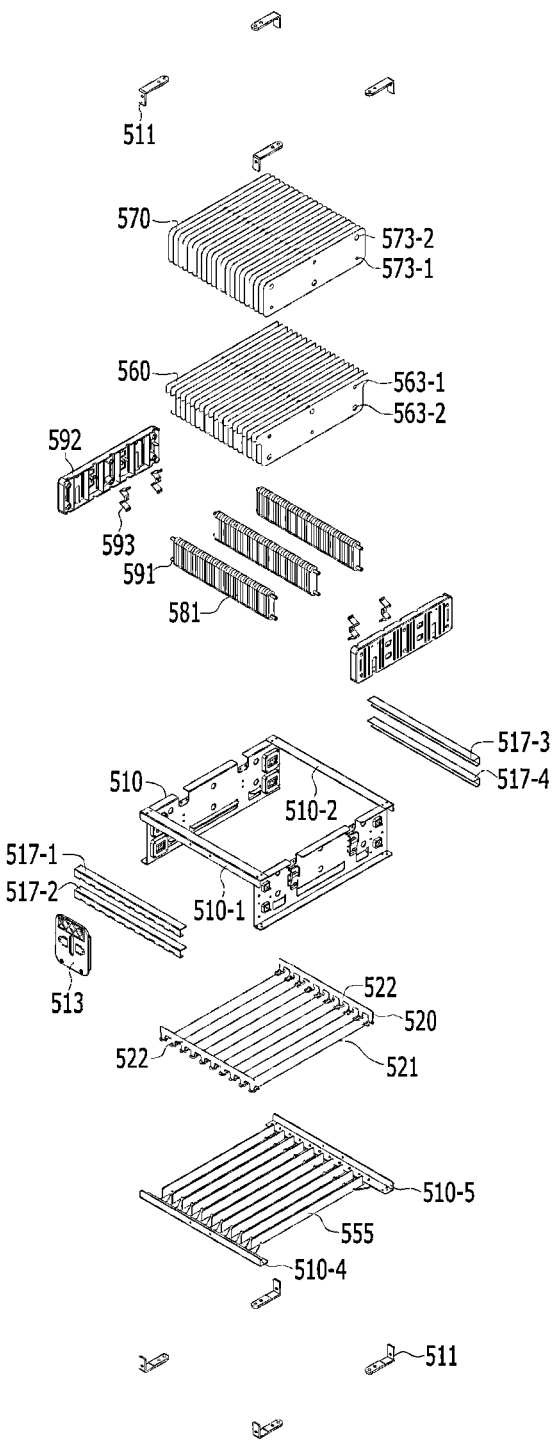

[Fig. 13]
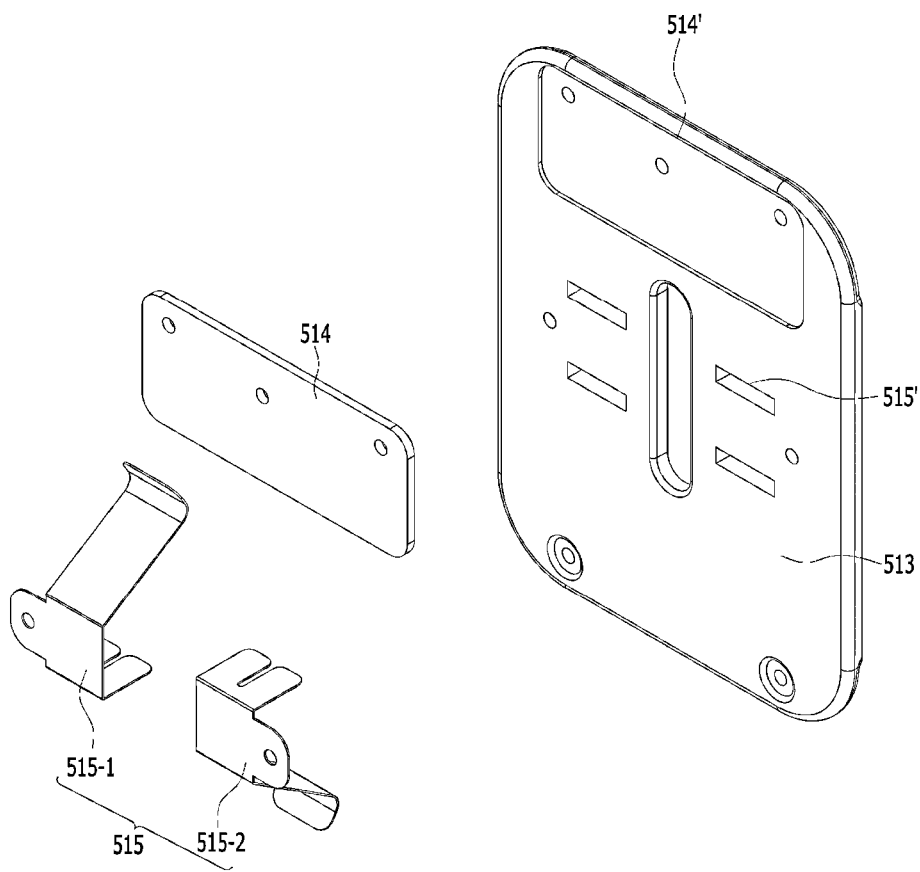

[Fig. 14]
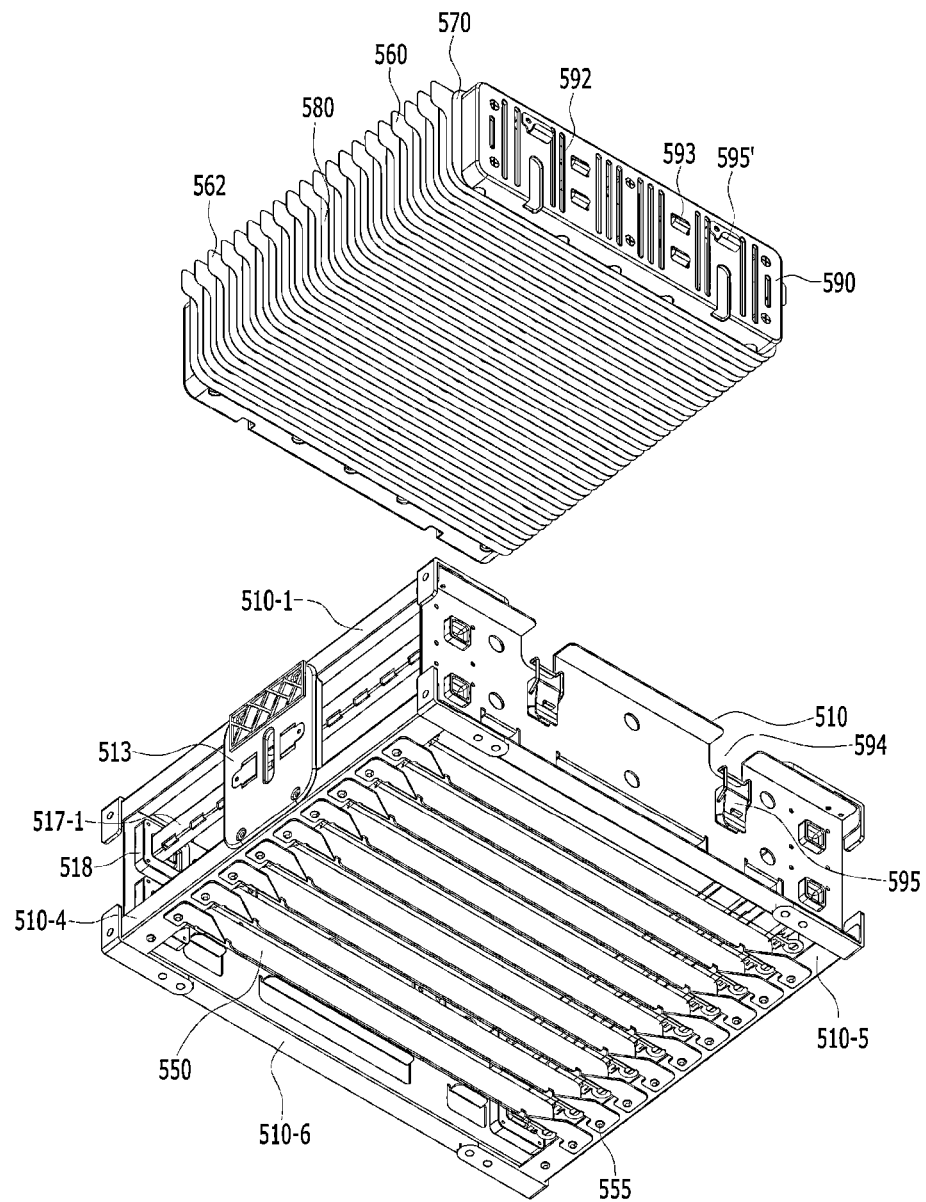

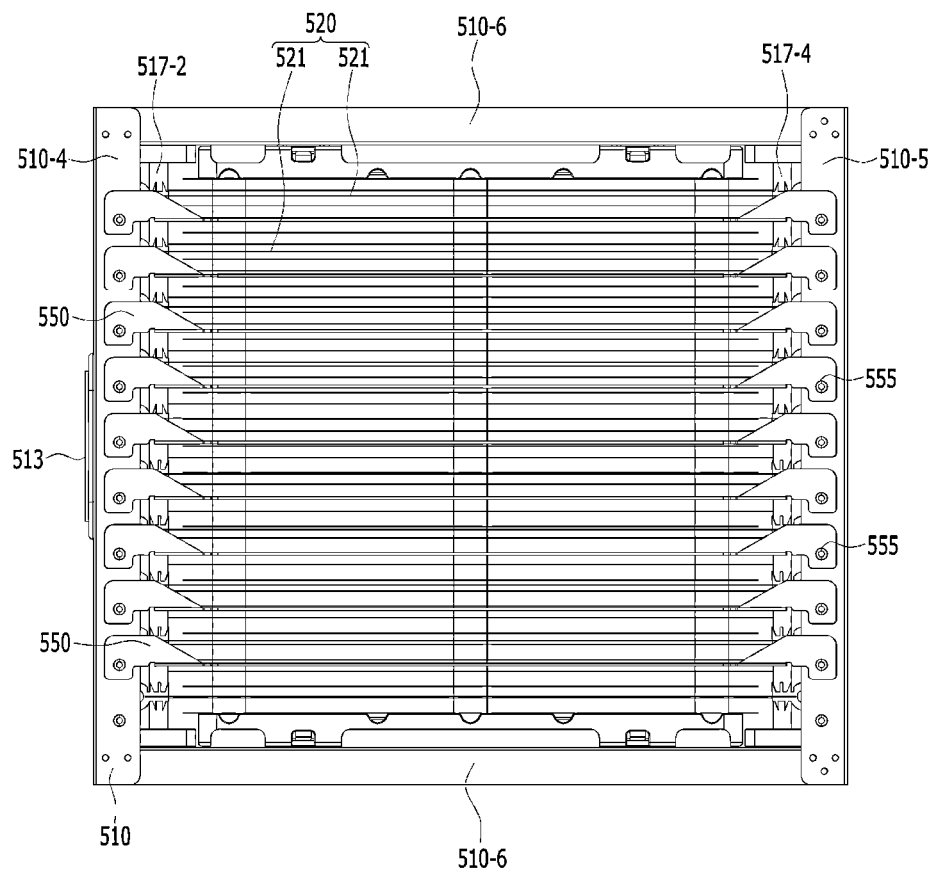
[Fig. 15]

[Fig. 16]
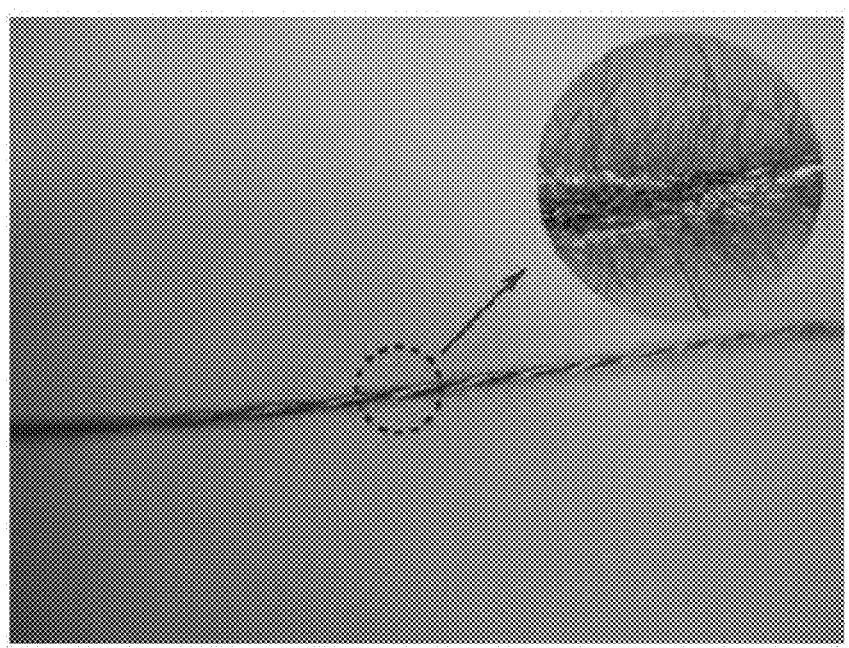

[Fig. 17]
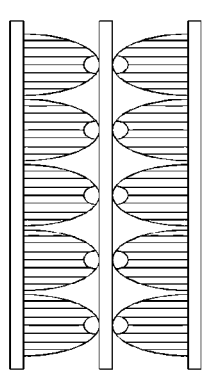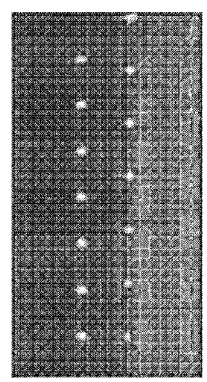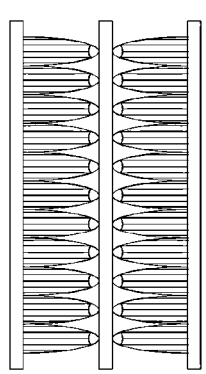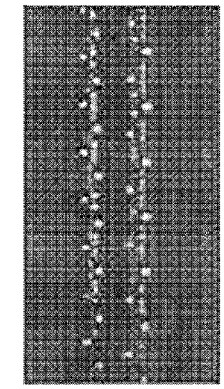
(a)  (b)

[Fig. 18]
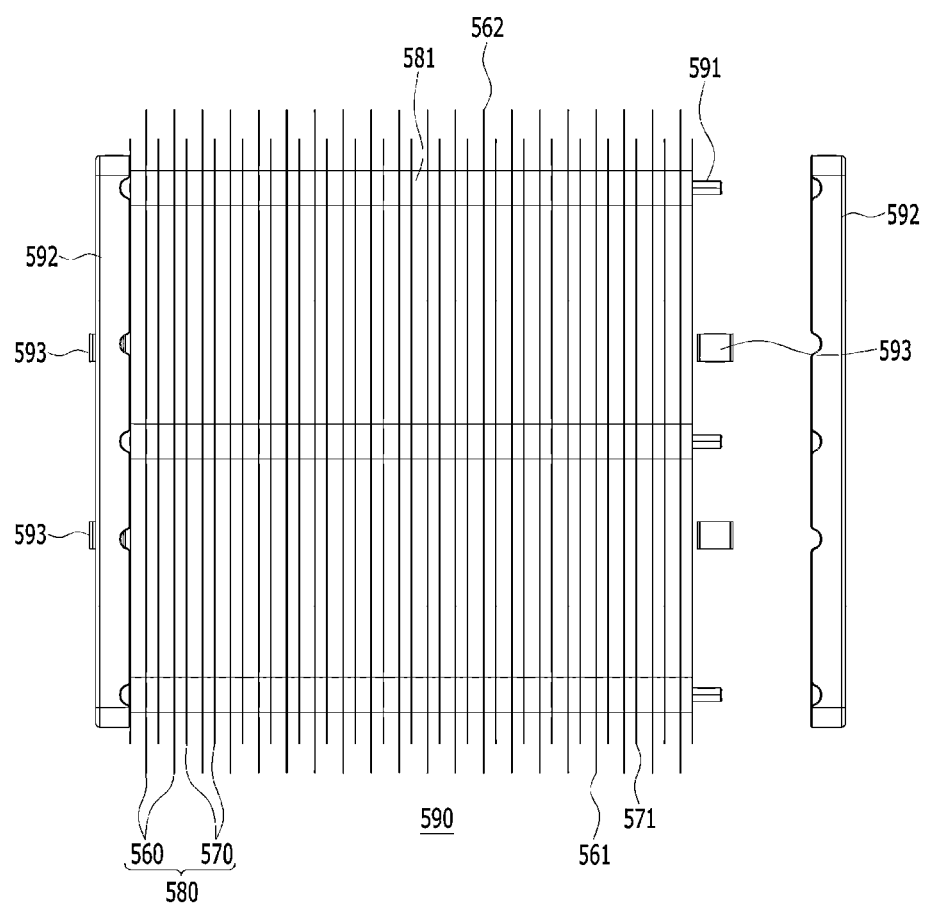

[Fig. 19]
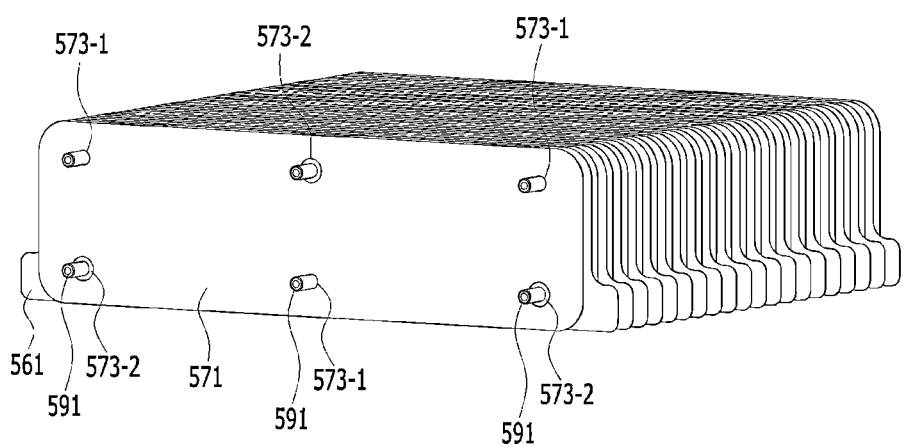

[Fig. 20]
(a) 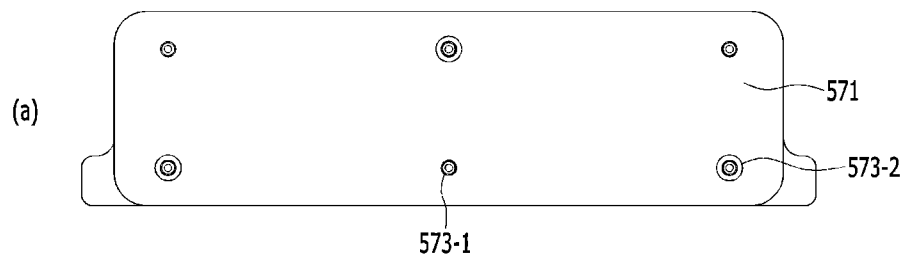
(b) 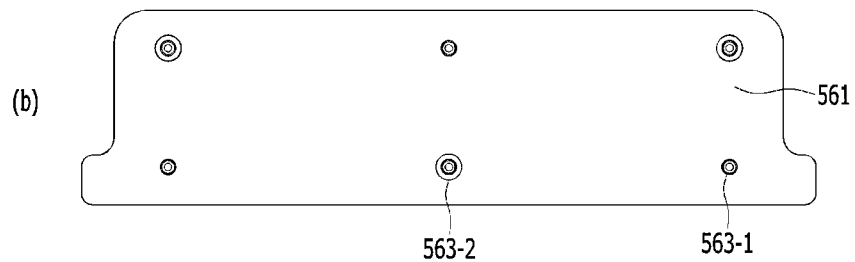

[Fig. 21]
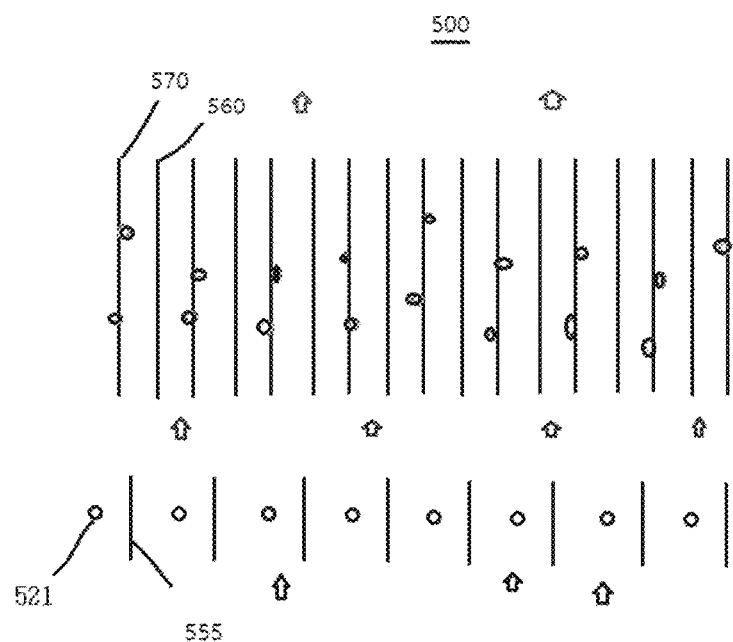

[Fig. 22]
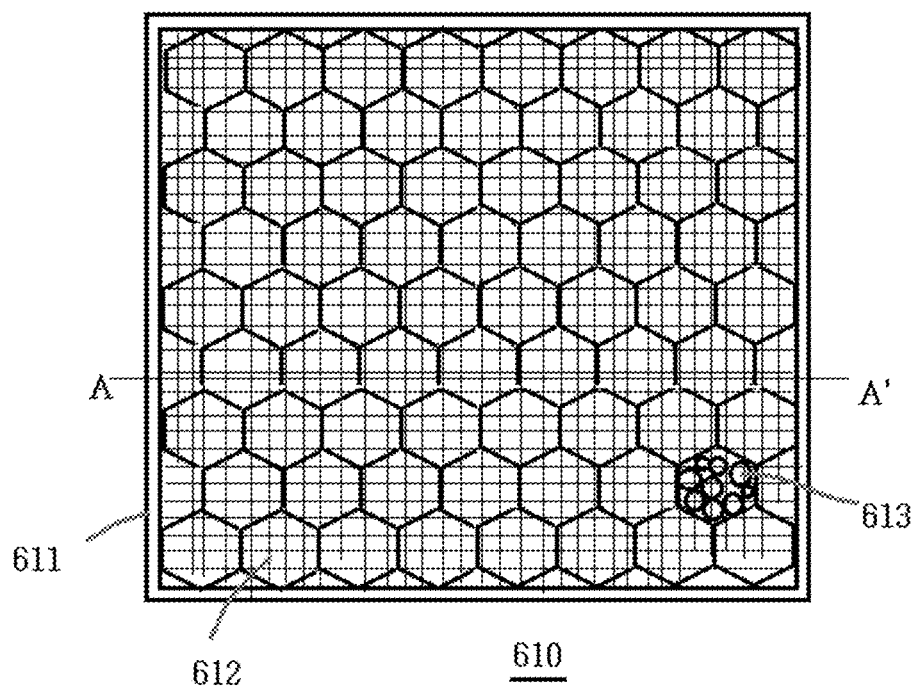

[Fig. 23]
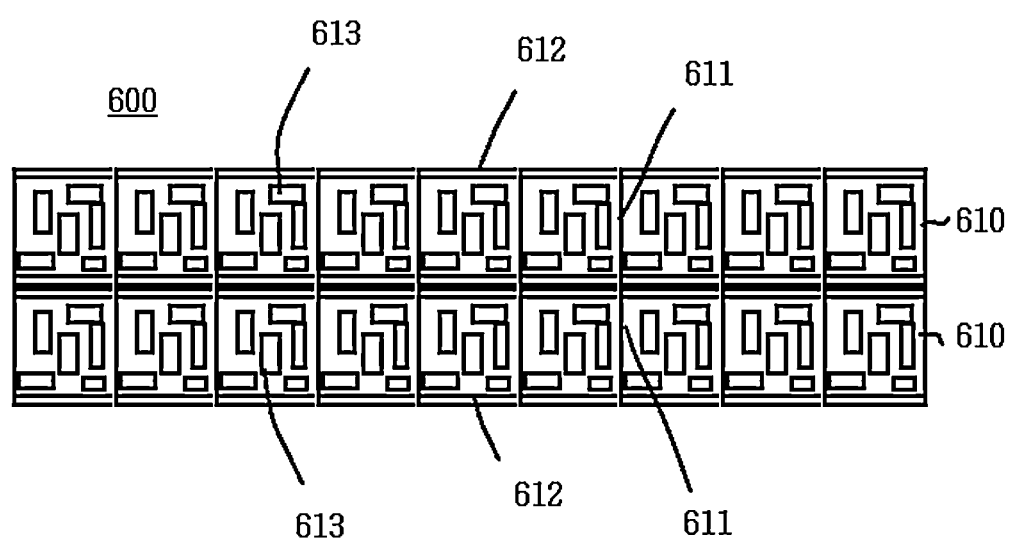

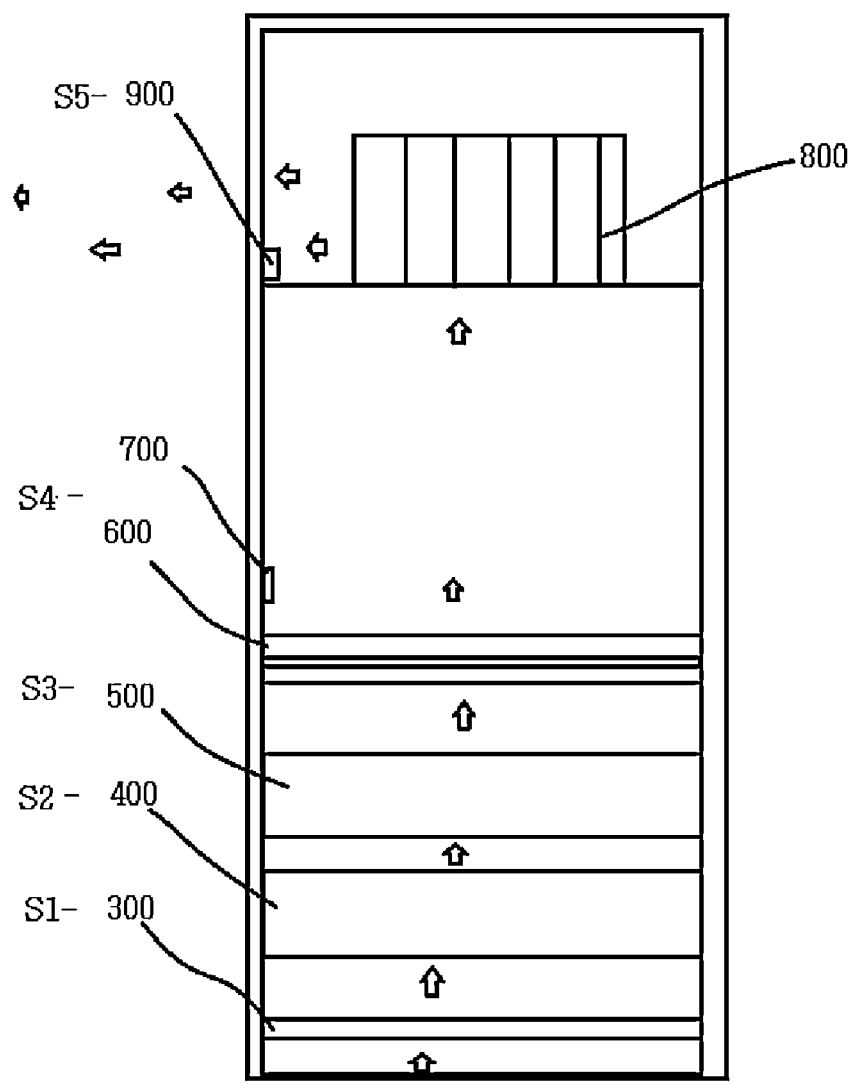
[Fig. 24]

AIR PURIFIER FOR IMPROVING REMOVAL PERFORMANCE OF HAZARDOUS SUBSTANCE AND VIRUS IN AIR

PRIORITY CLAIM

This application is a National Phase application filed under 35 USC § 371 of International Application No. PCT/KR2021/016479, filed on Nov. 12, 2021, which claims the benefit under 35 USC § 365 of prior filed Korean Patent Application Nos. 10-2020-0153516, filed Nov. 17, 2020, 10-2020-0167427, filed Dec. 3, 2020, and 10-2020-0189375, filed on Dec. 31, 2020, each of which is incorporated by reference in its entirety.

TECHNICAL FIELD

The present invention relates to an air purifier, and more specifically, to an air purifier that is capable of removing hazardous substances and viruses from air.

BACKGROUND ART

As diseases caused by viruses, such as coronavirus disease (COVID-19), have recently prevailed, demands for air purifiers capable of removing air pollutants such as fine particles as well as germs such as viruses, bacteria, and the like have increased.

An air purifier, which is disclosed in Korean Patent Application Laid-open No. 10-2007-0094026, includes a streamer discharge device disposed in an air path, a catalytic means activated by active species generated through streamer discharge, and a dust collection device.

In specific, a large amount of active species generated through the streamer discharge may damage the proteins or lipids of viruses contained in the air not treated to allow the viruses to become effectively non-activated, but unfortunately, the streamer discharge device decreases air flows and accompanies occurrence of ozone. Above all, if an ozone level is greater than 30 ppb, ozone may be harmful to a human body, and so as to allow the air purifier to be used in an indoor space, accordingly, the ozone generation problem has to be solved.

To solve such ozone generation problems, accordingly, a conventional air purifier, which is disclosed in Korean Patent Application Laid-open No. 10-2020-0064670 entitled 'Plasma sterilization module and air purifier having the same', is configured to improve a structure of a discharge device in which streamer discharge and glow discharge are combined with each other to thus achieve discharge efficiency improvement and ozone generation suppression.

In this case, however, all discharge electrodes are located in one space and thus influenced by one another, thereby failing to form uniform electric fields and decreasing discharge efficiency. Accordingly, ozone may be unintendedly generated when the air purifier is used for a long period of time or abnormally operates. Further, it is hard to remove the ozone once generated.

Besides, a glow discharge device serving to collect dust is installed together with a streamer discharge device, so that a streamer discharge area may be contaminated by means of the glow discharge.

DISCLOSURE

Technical Problem

Accordingly, the present invention has been made to solve the above-mentioned problems, and it is an object of the present invention to provide an air purifier that is capable of effectively solving efficiency reduction due to non-uniform electric fields, contamination occurrence due to discharge and dust collection, and generation of ozone.

It is another object of the present invention to provide an air purifying method that is capable of effectively solving efficiency reduction due to non-uniform electric fields, contamination occurrence due to discharge and dust collection, and generation of ozone.

Technical Solution

To accomplish the above-mentioned objects, according to one aspect of the present invention, there is provided an air purifier including: a body having an air inlet formed on a lower end thereof, an air outlet formed on an upper end thereof, and a flow path formed therein to move air upward; a pre-filter disposed in the flow path of the body; a box-shaped cell type discharge device disposed in the flow path of the body to generate active species; a dust collection device in the flow path of the body and having a discharge part with a linear discharge electrode and a dust collection part for collecting the dust charged through the discharge part; an ozone removal device in the flow path of the body to remove ozone generated from the discharge device and/or the dust collection device; and an air fan disposed in the flow path of the body.

Even though not theoretically limited, the air purifier according to the present invention may be configured to allow the box-shaped cell type discharge device generating the active species containing radicals to arrange needle-shaped discharge electrode plates on a plurality of cells to form uniform electric fields so that the active species are uniformly produced in the discharge device to suppress the ozone from being generated and to remove the generated ozone, thereby preventing the ozone from being emitted to an indoor space through the air outlet to provide safe and purified air to the indoor space.

According to the present invention, the body may have an opening formed on one side surface thereof to allow the box-shaped cell type discharge device and the dust collection device to be slidingly insertable and drawable thereinto and therefrom.

According to the present invention, the body may have support stands facing the inner walls thereof to allow the pre-filter, the discharge device, the dust collection device, and/or the ozone removal device to be slidingly insertable and drawable thereinto and therefrom.

According to the present invention, the pre-filter may be a mesh type filter or a filter having permeability corresponding to the mesh type filter to prevent dust, particles, and moisture from being introduced into the air purifier through the fan.

According to the present invention, the box-shaped cell type discharge device may be a streamer discharge device.

According to the present invention, the box-shaped cell type discharge device may include a first electrode plate on which the box-shaped cells with a given length are repeatedly connected vertically to one another and a second electrode plate adapted to locate the needle-shaped discharge electrode plates on the box-shaped cells.

According to the present invention, the box-shaped cell type discharge device may be a streamer discharge device.

According to the present invention, the box-shaped cells of the box-shaped cell type discharge device may have the same diameter as one another and rectangular sections with the same size as one another so as to form the uniform electric fields.

According to the present invention, the box-shaped cells may have holes formed on wall surfaces thereof to mix the active species between the neighboring box-shaped cells.

According to the present invention, each needle-shaped electrode plate may include a fixing plate located at the center of each box-shaped cell and a plurality of needles protruding from the fixing plate toward wall surface directions of the box-shaped cell.

According to the present invention, the needles may protrude from the fixing plate toward the holes formed on the wall surfaces of the cell.

According to the present invention, the side surfaces of the first electrode plate and the second electrode plate may be fixed to a box-shaped case whose top and underside are open to thus provide a discharge module.

According to the present invention, the box-shaped cell type discharge device may be a plasma module insertable into and drawable from the body.

According to the present invention, the dust collection device may include: the discharge part with the linear discharge electrode constituted of metal wires disposed side by side at given intervals and relative electrode plates disposed between the neighboring metal wires of the linear discharge electrode; and the dust collection part having a plurality of dust collection plates for collecting ionized particles exhausted from the discharge part.

According to the present invention, the metal wires of the linear discharge electrode may be nanowires, desirably yarn type metal wires made by twisting stainless nanowires.

According to the present invention, the side surfaces of the discharge part and the dust collection part may be fixed to a box-shaped case whose top and underside are open to thus provide a dust collection module.

According to the present invention, the dust collection device including the linear discharge electrode may be a dust collection module insertable into and drawable from the body.

According to the present invention, the ozone removal device may include an ozone removal catalytic device and an ozone removal light irradiation device, desirably a combination of the two.

According to the present invention, the ozone removal catalytic device may include catalytic plates as horizontal plates each having box-shaped cells connected to one another in left and right directions and filled with catalytic particles. The catalytic plates may have honeycomb-shaped cells as the box-shaped cells thereof and meshes disposed on top and underside thereof to allow the catalytic particles to escape and to permit air to permeate therethrough.

According to the present invention, the catalytic plates may be multi-layered, and the side surfaces of the catalytic plates may be fixed to a box-shaped case whose top and underside are open to thus provide a catalytic module. The catalytic particles are known manganese dioxide particles that are commercially purchased.

According to the present invention, the ozone removal light irradiation device may irradiate UV onto air. The UV may be irradiated through LEDs, and desirably, a plate on which UV LED chips are arranged may be attached to the inside of the body.

According to the present invention, the fan may be a general rotary fan that sucks air from the bottom of the air purifier and emits the air upward.

According to the present invention, the air purifier may further include a negative ion generation device disposed on the upper end thereof.

To accomplish the above-mentioned objects, according to another aspect of the present invention, there is provided an air purifying method including the steps of: flowing air into an air purifier; allowing the flowing air to pass through a box-shaped cell type discharge device for generating active species; allowing the flowing air to pass through a dust collection device having a linear discharge electrode; and removing ozone generated from the discharge device and/or the dust collection device.

According to the present invention, the air purifying method may further include the step of generating negative ions.

According to the present invention, the ozone removal step may include catalyst adsorption step and/or photodegradation step.

According to the present invention, the ozone removal step through the catalytic absorption may further include the step of removing moisture to protect a catalyst.

To accomplish the above-mentioned objects, according to still another aspect of the present invention, there is provided a plasma module insertable into and drawable from a body of an air purifier, including: a box-shaped case whose top and underside are open; a first electrode plate insulated from the box-shaped case and having a plate with a plurality of rectangular holes punched thereinto and needle-shaped electrode plates fixed to areas not punched on the plate; and a second electrode plate having a cell type plate with a plurality of box-shaped cells arranged horizontally on left and right sides, seated inside the box-shaped case to allow the needle-shaped electrode plates to be inserted into the box-shaped cells, and conductive with the box-shaped case.

According to the present invention, the box-shaped case of the plasma module may be a rectangular case that is slidingly insertable into the body having the shape of a rectangular parallelepiped and is made of conductive metal plates.

According to the present invention, the box-shaped case may include flanges or protruding pieces disposed on top and bottom ends and/or between top and bottom ends of both sides thereof, desirably on top and bottom ends of both sides thereof in an insertable/drawable direction, so as to conveniently perform sliding insertion and insulation from the body.

According to the present invention, the box-shaped case may include a ground terminal connected to a ground end of the body when inserted into the body and a high voltage terminal connected to a high voltage end of the body when inserted into the body.

According to the present invention, the box-shaped case may include the high voltage terminal and the ground terminal on an outer surface thereof, desirably, a front surface thereof, so that the high voltage terminal insulatedly passes through the box-shaped case and is conductive with the first electrode plate insulated from the box-shaped case, and the ground terminal comes into contact with the outer surface of the box-shaped case and is conductive with the second electrode plate coming into contact with inner surfaces of the box-shaped case.

According to the present invention, the plasma module may include insulation members fixed to the box-shaped case, desirably inner wall insulation members fixed to the inner walls of the box-shaped case, to allow the box-shaped case to be insulated from the first electrode plate.

According to the present invention, each inner wall insulation member may include an insulation body coupled to the box-shaped case and one or more insulation protrusions for fixing the first electrode plate and/or the second electrode plate thereto.

According to the present invention, the insulation protrusions may protrude inwardly from the insulation body so that the undersides thereof are coupled to the first electrode plate and the tops thereof are coupled to the second electrode plate. According to the present invention, the first electrode plate may be screw-fixed to the undersides of the insulation protrusions and the second electrode plate may be just seated onto the tops of the insulation protrusions.

According to the present invention, each inner wall insulation member may include one or more coupling protrusions coupled to the box-shaped case, and the coupling protrusions may protrude outwardly from the insulation body and be thus inserted into incised portions, holes or grooves formed on the box-shaped case.

According to the present invention, the coupling protrusions may be insertedly fixed to the incised portions formed on top of the box-shaped case to allow the plasma module to be easily separated from the box-shaped case.

According to the present invention, the first electrode plate may include a rectangular plate and needles, and the plate may include a plurality of rectangular holes punched arrangedly thereinto and needle-shaped electrode plates fixed vertically to areas not punched on the plate.

According to the present invention, the rectangular plate may be screw-fixed to the undersides of the insulation protrusions of the inner wall insulation members fixed to the inner wall of the box-shaped case.

According to the present invention, the needle-shaped electrode plates may have a plurality of needles protruding horizontally therefrom at given intervals along a height of a vertical plate thereof.

According to the present invention, the needle-shaped electrode plates may be located at the centers of the box-shaped cells of the second electrode plate.

According to the present invention, the first electrode plate may come into contact with the high voltage terminal passing through one side wall surface of the box-shaped case in a state of being fixed to the inner wall insulation members, so that a high voltage is applied thereto.

According to the present invention, the second electrode plate may include a cell type plate having a plurality of rectangular box-shaped cells arranged horizontally thereon in left and right sides. The rectangular box-shaped cells of the cell type plate may have the same shape and size as one another, for example, rectangular sections with the same size as one another so as to form uniform electric fields.

According to the present invention, the box-shaped cells may have mixing holes formed on wall surfaces thereof to mix the active species between the neighboring box-shaped cells. Desirably, the mixing holes may be formed to allow the needles formed on the needle-shaped electrode plates to face the centers thereof so as to achieve gentle mixing and discharge.

According to the present invention, the second electrode plate may be seated onto the insulation protrusions of the inner wall insulation members attached to the inner walls of the box-shaped case and spaced apart from the first electrode plate by a given distance, and the needle-shaped electrode plates of the first electrode plate are fixedly inserted into the corresponding rectangular box-shaped cells.

According to the present invention, the second electrode plate may include contact pins disposed on sides of the cell type plate thereof to come into contact with the inner walls of the box-shaped case, so that the contact pins are conductive with the ground terminal attached to the outer surface of the box-shaped case.

According to the present invention, the plasma module may further include body insulation members adapted to enable the box-shaped case to be insulated from the body. The body insulation members may be attached to the outer surfaces of the box-shaped case, desirably, to top, bottom, or sides of the box-shaped case, to prevent the box-shaped case excepting the high voltage terminal and the ground terminal from coming into contact with the body. Desirably, the body insulation members may be plastic members attached to tops and undersides of flanges formed on top and bottom side surfaces of the box-shaped case.

According to the present invention, the plasma module may be insulated from the body of the air purifier by means of the body insulation members, and accordingly, a power source may be applied to the plasma module only through the high voltage terminal and the ground terminal.

To accomplish the above-mentioned objects, according to yet still another aspect of the present invention, there is provided a dust collection module insertable into and drawable from a body of an air purifier, including: a box-shaped case whose top and underside are open; an ionization part disposed inside the box-shaped case and having a linear discharge electrode with metal wires disposed side by side at given intervals and relative electrode plates disposed between the neighboring metal wires of the linear discharge electrode; and a dust collection part disposed inside the box-shaped case and having a plate assembly with a plurality of discharge plates to which a high voltage is applied to collect ionized particles exhausted from the ionization part and dust collection plates disposed between the neighboring discharge plates.

According to the present invention, the dust collection module may include high voltage terminals coming into contact with high voltage terminals of the body and a ground terminal coming into contact with a ground terminal of the body.

According to the present invention, the high voltage terminals may be conductive with the linear discharge electrode of the ionization part and the discharge plates of the dust collection part, and the ground terminal may be conductive with the relative electrode plates of the ionization part and the dust collection plates of the dust collection part through the box-shaped case insulated from the high voltage terminals.

According to the present invention, the box-shaped case of the dust collection module may be a rectangular case that is slidingly insertable into the body having the shape of a rectangular parallelepiped and is made of conductive metal plates. The four surfaces of the rectangular case are all closed, and if necessary, otherwise, one or more surfaces thereof, for example, the front surface thereof in an insertion direction of the rectangular case may be open.

According to the present invention, the box-shaped case of the dust collection module may have flanges or protruding pieces formed on top and bottom ends of both sides thereof and/or between top and bottom ends thereof, desirably, on top and bottom ends of both sides thereof, so as to be conveniently insertable and drawable into and from the body.

According to the present invention, the box-shaped case of the dust collection module may include the ground terminal connected to the ground terminal of the body when inserted into the body and the high voltage terminals connected to the high voltage terminals of the body when inserted into the body.

According to the present invention, the high voltage terminals and the ground terminal may be disposed on the front surface of the box-shaped case, but if the front surface is open, the high voltage terminals and the ground terminal may be disposed on a docking plate fixed to the front surface, so that the high voltage terminals disposed on the docking plate are conductive with the linear discharge electrode of the ionization part and the discharge plates of the dust collection part.

According to the present invention, the docking plate may have a first high voltage terminal for the ionization part and a second high voltage terminal for the dust collection part, so that the first high voltage terminal insulatedly passes through the docking plate and comes into contact with the linear discharge electrode of the ionization part fixed insulatedly to the box-shaped case on the bottom of the box-shaped case, and the second high voltage terminal insulatedly passes through the docking plate and comes into contact with the discharge plates of the dust collection part fixed insulatedly to the box-shaped case on the top of the box-shaped case.

According to the present invention, the docking plate may have the ground terminal for the ionization part and the dust collection part, so that the ground terminal comes into contact with the box-shaped case and conductively comes into contact with the relative electrode plates of the ionization part fixed conductively to the box-shaped case and the dust collection plates of the dust collection part.

According to the present invention, the linear discharge electrode of the ionization part may include front transverse rods and rear transverse rods insulatedly disposed on both sides of the interior of the box-shaped case and the metal wires connecting the front transverse rods and the rear transverse rods with one another in parallel with one another. According to the present invention, the metal wires may be fixed one by one to the front transverse rods and the rear transverse rods. According to the present invention, the metal wires may be fixed to given metal supports parallel with one another, and next, the metal supports are coupled conductively to the front transverse rods and the rear transverse rods, respectively.

According to the present invention, the metal wires of the linear discharge electrode may be nanowires, desirably yarn type metal wires made by twisting stainless nanowires. According to the present invention, the high voltage terminals may come into contact with the front transverse rods to apply a high voltage to the nanowires.

According to the present invention, the relative electrode plates of the ionization part may be alternately fixed to the neighboring metal wires in vertical states to top of the box-shaped case. The relative electrode plates may be fixed conductively to top of the box-shaped case and be thus grounded through the ground terminal coming into contact with the box-shaped case.

According to the present invention, the dust collection part may be an integral type dust collection part that includes a plate assembly with a plurality of discharge plates to which a high voltage is applied and dust collection plates disposed between the neighboring discharge plates, a plurality of conductive through hole-passing bars passing through the plate assembly, and protection plates configured to allow the through hole-passing bars to be fixed to inner surfaces thereof and to allow the box-shaped case to be fixed to outer surfaces thereof.

According to the present invention, the protection plates may be insulation plates and have a plurality of holes for discharging water therethrough and hooks for coupling the dust collection module to the box-shaped case.

According to the present invention, the discharge plates may have the same shape as one another, and each discharge plate may be a rectangular plate having protrusions protruding forwardly and backwardly therefrom and through holes formed on the same position as one another. The protrusions of the discharge plates may come into contact with discharge electrodes fixed insulatedly to the interior of the box-shaped case to allow a high voltage to be applied thereto. Further, some of the through holes of the discharge plates may have the corresponding diameter to the through hole-passing bars, and the rest have the diameter greater than the through hole-passing bars. Accordingly, only some of the through hole-passing bars passing through the discharge plates come into contact with the discharge plates, so that the discharge plates can be conductive with one another.

According to the present invention, the dust collection plates may have the same shape as one another, and each dust collection plate may be a rectangular plate having through holes formed on the same position as the discharge plated. Further, some of the through holes of the dust collection plates have the corresponding diameter to the through hole-passing bars, and the rest have the diameter greater than the through hole-passing bars. Accordingly, only some of the through hole-passing bars passing through the dust collection plates come into contact with the dust collection plates, so that the dust collection plates can be conductive with one another.

According to the present invention, the dust collection plates may be located on both sides of the plate assembly, and ground terminals are attached to both side duct collection plates, so that the ground terminals pass through holes formed on the protection plates and are conductive with the box-shaped case.

According to the present invention, the plasma module may further include body insulation members adapted to enable the box-shaped case to be insulated from the body. The body insulation members may be attached to the outer surfaces of the box-shaped case, desirably, to top, bottom, or sides of the box-shaped case, to prevent the box-shaped case excepting the high voltage terminals and the ground terminal from coming into contact with the body. Desirably, the body insulation members may be plastic members attached to tops and undersides of flanges formed on top and bottom side surfaces of the box-shaped case. According to the present invention, the dust collection module may be insulated from the body of the air purifier by means of the body insulation members, and accordingly, a power source is applied to the dust collection module only through the high voltage terminals and the ground terminal.

Advantageous Effects

According to the present invention, the air purifier can be configured to allow uniform electric fields to be formed through the box-shaped cell type discharge device, thereby enhancing treatment efficiency and reducing ozone emission.

According to the present invention, further, the plasma module insertable into and drawable from the body of the air purifier can be configured to allow the needles to be arranged in the cells, respectively, thereby reducing the interference among the needles to form uniform electric fields, enhancing treatment efficiency, and providing easy washing and maintenance.

According to the present invention, further, the dust collection module insertable into and drawable from the body of the air purifier can be configured to be easily detached from the body and conveniently washed.

DESCRIPTION OF DRAWINGS

FIG. 1 is a perspective view showing an outer appearance of an air purifier according to the present invention.

FIG. 2 is a rear view showing the air purifier according to the present invention.

FIG. 3 is an exploded perspective view showing the air purifier according to the present invention, which is viewed in a front surface direction thereof.

FIG. 4 is an exploded perspective view showing the air purifier according to the present invention, which is viewed in a rear surface direction thereof.

FIG. 5 is a perspective view showing an insertable/drawable plasma module according to the present invention.

FIG. 6 is a perspective view showing the underside of the insertable/drawable plasma module viewed in the opposite direction to that of FIG. 5, from which an external insulation member is removed.

FIG. 7 is a perspective view showing the insertable/drawable plasma module viewed in the opposite direction to that of FIG. 6, from which the external insulation member is removed and a rectangular case is separated.

FIG. 8 is a perspective view showing a first electrode plate of the insertable/drawable plasma module.

FIG. 9 is a perspective view showing a second electrode plate of the insertable/drawable plasma module.

FIG. 10 is a schematic view showing coupling relations of the insertable/drawable plasma module.

FIG. 11 is a perspective view showing an insertable/drawable dust collection module according to the present invention.

FIG. 12 is an exploded perspective view showing the insertable/drawable dust collection module.

FIG. 13 is an exploded perspective view showing a docking plate attached to the front side of the insertable/drawable dust collection module.

FIG. 14 is an exploded underside perspective view showing a dust collection part of the insertable/drawable dust collection module.

FIG. 15 is a bottom view showing the insertable/drawable dust collection module.

FIG. 16 is an enlarged photograph showing a metal wire of the air purifier according to the present invention.

FIGS. 17a and 17b are schematic views showing discharged states of metal wires, wherein FIG. 7a shows an existing tungsten metal wire, and FIG. 7b shows a nanowire according to the present invention.

FIG. 18 is a photograph showing an integral type dust collection part of the insertable/drawable dust collection module, from which one side protection cover is removed.

FIG. 19 is a perspective view showing a state where unit dust collection plates and unit discharge plates coaxially arranged to each other are penetrated.

FIGS. 20a and 20b are side views showing the state where the unit dust collection plates and the unit discharge plates are coaxially arranged to each other, wherein FIG. 20a shows the unit dust collection plate is located on a front surface, and FIG. 20b shows the unit discharge plate is located on the front surface.

FIG. 21 is a schematic view showing an operating state of the dust collection module.

FIG. 22 is a plan view showing an ozone removal catalytic device of the air purifier according to the present invention.

FIG. 23 is a sectional view taken along the line AA' of FIG. 22.

FIG. 24 is an exemplary view showing air purifying steps according to the present invention.

BEST MODE FOR INVENTION

Hereinafter, the present invention will be described in detail with reference to the attached drawings. Before the present invention is disclosed and described, it is to be understood that the disclosed embodiments are merely exemplary of the invention, which can be embodied in various forms.

As shown in FIGS. 1 to 4, an air purifier 10 according to the present invention includes a generally rectangular body 100 having a front surface 110, side surfaces 120, a rear surface 130, a bottom surface 140, and a top surface 150.

Further, an air outlet 111 is formed on an upper portion of the front surface 110, and an air inlet 142 is formed on the bottom surface 140. After air is introduced through the air inlet 142, it moves upward in an interior of the body 100, is purified, and is then exhausted through the air outlet 111.

An exhaust cover 112 is attached to the air outlet 111 formed on the upper portion of the front surface 110 to adjust the direction of air exhausted to every direction, and a control panel 113 for controlling operations of the air purifier 10 and a panel substrate 114 are disposed on the upper portion of the front surface 110.

The front surface 110 and the side surfaces 120 are formed unitarily with each other by bending a single rectangular plate to a U-like sectional shape.

The rear surface 130 has an opening and closing part 131 separable from the body 100 if necessary.

The bottom surface 140 is made of a rectangular plate and has the air inlet 142 formed on the central portion thereof and casters 141 attached to the underside thereof, so that the air purifier 10 can be spaced apart from a floor.

Further, the air purifier 10 according to the present invention includes an internal bracket 200 disposed inside the body 100 to install modularized treatment devices therein.

The internal bracket 200 has the shape of a rectangular parallelepiped with a size insertable into the body 100 and a height from the bottom end of the body 100 to the bottom end of the air inlet 112.

The internal bracket 200 is closed on a front surface 210 and side surfaces 220 whose some portions are open, is open on bottom and top surfaces thereof, and has a rear surface 230 with an insertable and drawable hole 231 into and from which modularized treatment devices are insertable and drawable. Further, a plurality of insertable and drawable stands 232 are located in the insertable and drawable hole 232 to allow the modularized treatment devices to be slidingly insertable into and drawable from the insertable and drawable hole 232. The internal bracket 200 has a semicircular inducing plate 250 disposed on top thereof to gently execute air therealong.

The modularized treatment devices, which are insertable into and drawable from the internal bracket 200, include a pre-filter 300 disposed on bottom thereof to filter large dust, a box-shaped cell type discharge device 400 disposed above the pre-filter 300 to generate active species including radicals, a dust collection device 500 disposed above the box-shaped cell type discharge device 400, and an ozone removal catalytic device 600 disposed above the dust collection device 500 to absorb and remove ozone.

Further, an ozone removal light irradiation device 700 is attached to the form of a printed circuit board above the ozone removal catalytic device 600 in the internal bracket 200 so as to irradiate UV light, and an air fan 800 is disposed on top of the internal bracket 200 to suck air from the inside of the inducing plate 250 and execute the sucked air.

Additionally, a negative ion generation device 900 is disposed on the air outlet 111 to add negative ions to the air executed by the air fan 800.

A thin plate-like sponge pre-filter is used as the pre-filter 300 so that it can be disposed on the bottom end of the internal bracket 200.

As shown in FIGS. 5 to 10, the box-shaped cell type discharge device 400 includes: a rectangular case 410 open on top and underside thereof and made of conductive metal plates; a first electrode plate 420 having a plate 421 insulated from the rectangular case 410, fixed to an internal bottom end of the rectangular case 410, and a plurality of rectangular holes punched thereinto and needle-shaped electrode plates 423 fixed to areas not punched on the plate 421; and a second electrode plate 430 fixed to an internal top end of the rectangular case 410 to allow the needle-shaped electrode plates 423 to be inserted into cells thereof and conductive with the rectangular case 410.

The rectangular case 410 has flanges 412 extended from tops and undersides of side plates 411 parallel to an insertable and drawable direction among the side plates thereof in the insertable and drawable direction so as to improve conveniences in insertable and drawable operations and the insulation from the body 100. Further, the side plates 411 have incised portions 413 formed on tops thereof to fix first inner wall insulation members 480 thereto and bent pieces 414 disposed bent outward from the bottom ends of the incised portions 413.

The rectangular case 410 has a ground terminal 450 and a high voltage terminal 460 disposed on a front side surface thereof so that when the rectangular case 410 is inserted into the body 100, the ground terminal 450 is connected to a ground end of the body 100 and the high voltage terminal 460 to a high voltage end of the body 100.

The high voltage terminal 460 passes through the wall surface of the rectangular case 410, protrudes inwardly therefrom, and comes into contact with the underside of the first electrode plate 420, so that a high voltage is applied to the first electrode plate 420. The ground terminal 450 comes into contact with the outer surface of the rectangular case 410 and comes into contact with the inner surface of the rectangular case 410 by means of contact pins 431 of the second electrode plate 430, so that it grounds the second electrode plate 430.

The rectangular case 410 has body insulation members 440 disposed on top and bottom corners thereof so that it can be insulated from the body 100. A corner cover made of plastic and having a '¬'-shaped side section is used as each body insulation member 440.

The first inner wall insulation members 480 and second inner wall insulation members 485 are fixed to the inner walls of the rectangular case 410 to prevent the first electrode plate 421 from coming into contact with the inner walls of the rectangular case 410.

Each first inner wall insulation member 480 has a first insulation body 481-1 extended up and down, a first insulation protrusion 481-2 protruding inwardly from bottom thereof, and a coupling protrusion 481-3 protruding outwardly from top thereof. In specific, the first insulation bodies 481-1 are screw-fixed to the inner walls of the rectangular case 410, the plate 421 of the first electrode plate 420 is screw-fixed to the undersides of the first insulation protrusions 481-2, and the underside of the second electrode plate 430 is seated on tops of the first insulation protrusions 481-2, while being spaced apart from the first electrode plate 420. The coupling protrusions 481-3 are insertedly mounted on the incised portions 413 of the rectangular case 410, and the undersides of the coupling protrusions 481-3 are seated onto the bent pieces 414 protruding from the incised portions 413.

The coupling protrusions 481-3 seated onto the bent pieces 414 are firmly fixed by means of locking hooks attached to both side surfaces of the rectangular case 410.

Each second inner wall insulation member 485 has a second insulation body 485-1 extended up and down and a second insulation protrusion 485-2 protruding inwardly therefrom. The second insulation bodies 485-1 are fixed to the bottoms of the inner walls of the rectangular case 410, and the second insulation protrusions 485-2 are fixed to the same height as the first insulation protrusion 481-2. Further, the plate 421 of the first electrode plate 420 is screw-fixed to the undersides of the second insulation protrusions 485-2, and the underside of the second electrode plate 430 is seated on tops of the second insulation protrusions 485-2, while being spaced apart from the first electrode plate 420.

The first electrode plate 420 includes the rectangular plate 421 with the plurality of rectangular holes 425 arrangedly punched thereinto and the needle-shaped electrode plates 423 vertically fixed to the areas 426 not punched on the rectangular plate 421 and located between the rectangular holes 425.

The rectangular plate 421 has insulation member fixing holes 429 formed on the edges thereof to fix the undersides of the first insulation protrusions 481-1 of the first inner wall insulation members 481 and the undersides of the second insulation protrusions 485-1 of the second inner wall insulation members 485 thereto.

Further, the rectangular plate 421 has needle fixing holes 428 alignedly punched thereinto at given intervals on the areas 426 not punched thereon to fix the needle-shaped electrode plates 423 thereto. The needle fixing holes 428 may be varied in position according to cell positions of the second electrode plate 420, and they are located at the centers of the cells.

Each needle-shaped electrode plate 423 fixed to the rectangular plate 421 includes a vertical plate 422, a plurality of needles 424 protruding horizontally therefrom at given intervals along a height of the vertical plate 422, and a needle fixing piece 422' bent horizontally from the bottom thereof, so that the needle-shaped electrode plates 423 are fixed to the needle fixing holes 428, respectively. The number of needle-shaped electrode plates 423 corresponds to the number of cells of the second electrode plate 420 to allow discharge to be generated every cell, and the needle-shaped electrode plates 423 are not installed on areas where no discharge is needed, for example, edge portions where air flows rarely exist.

The second electrode plate 430 includes a cell type plate 432 having box-shaped cells 431 with rectangular sections connected to one another in a zigzag way, mixing holes 433 formed on the wall surfaces of the box-shaped cells 431, and contact pins 434 attached to the front and rear outer walls of the cell type plate 432.

The mixing holes 433 are formed plurally on one box-shaped cell 431, and to allow two cells to communicate with each other through one hole, the mixing holes 433 are formed on the wall surface and the corner of one box-shaped cell 431, respectively. Further, two or three mixing holes 433 are formed spaced apart from one another at given intervals to correspond to the heights of the needles 424 fixed to the first electrode plate 420.

The second electrode plate 430 is seated onto the top surfaces of the first insulation protrusions 481-2 of the first inner wall insulation members 481 and the top surfaces of the second insulation protrusions 495-2 of the second inner wall insulation members 485 and is thus spaced insulatedly apart from the first electrode plate 420 coupled to the undersides of the first insulation protrusions 481-2 and the undersides of the second insulation protrusions 485-2.

The second electrode plate 430 is prevented from moving upward by means of a fixing ring 470 fixed to tops of the first inner wall insulation members 481 and having the corresponding shape to the inner edges of the rectangular case 410. The fixing ring 470 is fixed to tops of the first inner wall insulation members 481 by means of screws.

The contact pins 434 of the second electrode plate 430 come into contact with the inner walls of the rectangular case 410, when the second electrode plate 430 is seated onto the first inner wall insulation members 481 and the second inner wall insulation members 485, and are electrically conductive with the rectangular case 410, so that they are electrically connected with the ground terminal 450 disposed on the outer wall of the rectangular case 410.

As shown in FIGS. 10 to 20, the insertable and drawable dust collection device 500 according to the present invention includes: an ionization part 550 having a rectangular parallelepiped-shaped box-shaped case 510 whose top and bottom are open, a linear discharge electrode 520 having metal wires 521 disposed side by side at given intervals, and relative electrode plates 555 disposed between the neighboring metal wires 521 of the linear discharge electrode 520; and a dust collection part 590 having a plate assembly 580 with a plurality of discharge plates 560 to which a high voltage is applied to collect ionized particles discharged from the ionization member 550 and dust collection plates 570 disposed between the neighboring discharge plates 560.

The ionization part 550 disposed on the bottom of the dust collection device 500 generates positive corona so as to allow the particles introduced therebelow to be charged positively, and the dust collection part 590 disposed on the top of the dust collection device 500 serves to allow the positively charged particles to be attachedly collected to the dust collection plates 570 charged negatively.

The box-shaped case 510 has the shape of the rectangular parallelepiped whose top and bottom are open, and further, the front surface thereof is open. The box-shaped case 510 has a front top edge 510-1, a rear top edge 510-2, both side top edges 510-3, a front bottom edge 510-4, a rear bottom edge 510-5, and both side bottom edges 510-6 and has four top corners at which the top edges meet and four bottom corners at which the bottom edges meet.

Further, the box-shaped case 510 has plastic insulation members 511 located on the four top corners and the four bottom corners and coupled to flanges thereof by means of screws to perform the insulation from the body 100 of the air purifier and the sliding operation toward the interior of the body 100.

The box-shaped case 510 has a docking plate 513 attached to the front surface thereof and connected to the ground terminal and the high voltage terminal of the body 100. A ground plate 514 is fixed to the upper portion of the docking plate 513, and two high voltage terminals 515 are disposed on the middle portion of the docking plate 513.

The ground plate 514 has the shape of a flat plate and is seated onto a ground plate seating portion 514' formed on the front surface of the upper portion of the docking plate 513 and thus fixed to the front top edge 510-1 of the box-shaped case 510 by means of rivets, together with the docking plates 513, so that the ground plate 514 is conductive with the box-shaped case 510.

The two high voltage terminals 515 are bent to the shape of '⊏', extended up and down, respectively, and inserted into high voltage terminal grooves 515' formed on the docking plate 513, respectively.

The box-shaped case 510 has transverse rods 517 transversely disposed in the interior thereof and made of a conductive material. Four transverse rods 517 are disposed on the front top and bottom portions and the rear top and bottom portions of the box-shaped case 510, respectively. In specific, the conductive transverse rods 517 include the front top transverse rod 517-1, the front bottom transverse rod 517-2, the rear top transverse rod 517-3, and the rear bottom transverse rod 517-4, and accordingly, both ends of each conductive transverse rod 517 are insertedly fixed to grooves formed on insulation brackets 518 passing through the left and right side walls of the box-shaped case 510 and thus fixed to the box-shaped case 510, so that the conductive transverse rods 517 are insulated from the box-shaped case 510.

The front top transverse rod 517-1 and the front bottom transverse rod 517-2 of the conductive transverse rods 517 come into contact with the two high voltage terminals 515 passing through the docking plate 513, respectively, and accordingly, they apply high voltages to objects electrically conductive therewith.

The ionization part 550 includes the linear discharge electrode 520 having the metal wires 521 disposed side by side at given intervals, front and rear ends of which are fixed to metal support rods 522 in parallel with one another, and the relative electrode plates 555 made of a metal and disposed between the neighboring metal wires 521 at given intervals, front and rear ends of which are fixed to the front bottom edge 510-4 and the rear bottom edge 510-5 in parallel with one another.

The metal wires 521 of the linear discharge electrode 520 of the ionization part 550 are conductive because the metal support rod 522 is fixed to the front bottom transverse rod 517-2, and as the front bottom transverse rod 517-2 comes into contact with the high voltage terminal 515-2 extended downward of the two high voltage terminals 515 fixed to the docking plate 513 and is thus conductive. The high voltage terminals 515 come into contact with the high voltage end of the air purifier, so that a high voltage is applied to the high voltage terminals 515.

The relative electrode plates 555 of the ionization part 550 are conductive because the front and rear ends thereof are fixed to the front bottom edge 510-4 and the rear bottom edge 510-5 of the box-shaped case 510, and they are grounded on the ground terminal of the body 100 through the ground plate 514 fixed to the front top edge 510-1 by means of the rivets passing through the front top edge 510-1 of the box-shaped case 510.

The dust collection part 590 includes the plate assembly 580 with the plurality of discharge plates 560 electrically conductive with the high voltage terminal of the body 100, to which a high voltage is thus applied, and the dust collection plates 570 arranged alternately with the discharge plates 560, electrically conductive with the high voltage terminal of the body 100, and thus grounded.

Each discharge plate 560 has a curved discharge protrusion 562 protruding from tops of the front and rear portions thereof and a rectangular unit discharge plate 561 with a plurality of discharge plate through holes 563, and the through holes 563 of the unit discharge plate 561 include first discharge through holes 563-1 each having a first diameter D1 and second discharge through holes 563-2 each having a second diameter D2 larger than the first diameter D1.

Each dust collection plate 570 has a rectangular unit dust collection plate 571 with a plurality of dust collection plate through holes 573, and the through holes 573 of the unit dust collection plate 571 includes first dust collection through holes 573-1 each having the first diameter D1 and second dust collection through holes 573-2 each having the second diameter D2.

The first discharge through holes 563-1 and the second dust collection through holes 573-2 are coaxially arranged, and the second discharge through holes 563-2 and the first dust collection through holes 573-1 are coaxially arranged. Further, through hole-passing bars 591 each having the corresponding diameter to the first diameter D1 pass through the through holes 563 and 573 in left and right directions. Accordingly, the through hole-passing bars 591 passing through the first discharge through holes 563-1 and the second dust collection through holes 573-2 aligned with one another come into contact only with the unit discharge plates 561, and the through hole-passing bars 591 passing through the second discharge through holes 563-2 and the first dust collection through holes 573-1 aligned with one another come into contact only with the unit dust collection plates 571.

Further, insulation spacing members 582 are disposed between the neighboring unit discharge and dust collection plates 561 and 571 of the plate assembly 580.

The plate assembly 580 is configured to allow the number of unit dust collection plates of the dust collection plates 570 to be one more than the number of unit discharge plates of the discharge plates 560, so that the dust collection plates 570 are located on both sides thereof.

Further, insulating protection plates 592 are located on both sides of the plate assembly 580, and both ends of each through hole-passing bar 591 are insertedly fixed to the insides of the insulating protection plates 592, thereby providing the integral type dust collection part 590.

The unit dust collection plates 571 located on both sides of the plate assembly 580 have ground protrusions 593 protruding from the surface facing the protection plates 592, passing through the protection plates 592, and protruding from both sides of the protection plates 592.

Further, the protection plates 592 have locking protrusions 595' protruding outwardly therefrom so that the locking protrusions 595' are exposed to the outside through incised portions 594 formed both sides of the box-shaped case 510, and next, the locking protrusions 595' are firmly fixed to the incised portions 594 by means of locking hooks 595 attached to outer surfaces of both sides of the box-shaped case 510.

The integral type dust collection part 590 is configured to allow the discharge protrusions 562 of the unit discharge plates 561 to protrude in forward and backward directions and to allow the discharge protrusions 562 to come into contact with the front bottom transverse rod 517-2 conductive with the high voltage terminals 515 fixed to the docking plate 513 and to be thus connected to the high voltage terminal of the body 100. Further, the integral type dust collection part 590 is configured to allow the unit discharge plates 561 to be electrically conductive with one another by means of the through hole-passing bars 591.

Moreover, the integral type dust collection part 590 is configured to allow the unit dust collection plates 571 to be electrically conductive with one another by means of the through hole-passing bars 591, to allow the unit dust collection plates 571 located on both sides of the plate assembly 580 to be grounded on the inner walls of the box-shaped case 510 by means of the ground protrusions 593 and to be thus connected to the ground terminals connected to the docking plate 513 attached to the box-shaped case 510.

Accordingly, the ionized particles through the ionization part 550 are collected on the unit dust collection plates 571 of the dust collection part 590. If dust is collected onto the unit dust collection plates 571 to make the unit dust collection plates 571 contaminated, the dust collection part 590 is separated from the dust collection device 500 by loosening the locking hooks 595, and the separated dust collection part 590 is washed with water and then dried.

Air passing through the dust collection device 500 contains ozone produced in the treatment processes, and to remove the ozone, accordingly, the air flows to the ozone removal catalytic device 600 disposed above the dust collection device 500.

As shown in FIG. 22, the ozone removal catalytic device 600 includes honeycomb plates 610 each having a filling plate 611 constituted of honeycomb-shaped cells, meshes 612 disposed on top and underside thereof, and ozone removal catalytic particles 613 filled in the cells. The ozone removal catalytic particles 613 are spherical and/or cylindrical manganese dioxide particles, which are commercially purchased. As shown in FIG. 23, the ozone removal catalytic converter 600 includes desirably one or more honeycomb plates 610, more desirably two honeycomb plates 610.

As shown in FIG. 24, the air purifier 10 according to the present invention operates in the following order. If the air purifier 10 works, first, the air fan 800 located on the upper portion thereof operates to thus form upward air flows inside the air purifier 10, and accordingly, contaminated air is introduced into the air purifier 10 through the lower portion thereof.

Step S1 is carried out so that the introduced air passes through the pre-filter 300 to remove dust therefrom.

Step S2 is carried out so that the air from which the dust is removed through step S1 passes through the box-shaped cell type discharge device 400 to allow viruses and germs contained in the air to be killed by means of active species such as radicals generated by streamer discharge.

Next, step S3 is carried out so that the air from which the viruses and/or germs are killed through step S2 passes through the dust collection device 500 to collect the components such as fine particles contained in the air that are not filtered through the pre-filter 300 and are not killed through the box-shaped cell type discharge device 400.

After that, step S4 is carried out so that the collected air passes through the ozone removal catalytic device 600 and the ozone removal light irradiation device 700 to remove ozone generated during the processes up to step S3. In step S4, ozone is attached to the ozone removal catalytic device 600, is converted into oxygen, and is then detached from the ozone removal catalytic device 600. The remaining ozone after the removal is converted into oxygen through the ozone removal light irradiation device 700.

Lastly, step S5 is carried out so that the air after step S4 is mixed with negative ions generated from the negative ion generation device 900, while being exhausted to the outside through the air fan 800.

- 10: Air purifier
- 100: Body
- 200: Internal bracket
- 300: Pre-filter
- 400: Box-shaped cell type discharge device
- 500: Dust collection device
- 600: Ozone removal catalytic device
- 700: Ozone removal light irradiation device
- 800: Air fan
- 900: Negative ion generation device

The invention claimed is:

1. An air purifier for removing viruses, comprising:
a body having an air inlet formed on a lower end thereof, an air outlet formed on an upper end thereof, and a flow path formed therein to move air upward;
a pre-filter disposed in the flow path of the body;
a modular type box-shaped cell type discharge device disposed in the flow path of the body to generate active species containing radicals so as to kill the viruses in the air and having a first electrode plate on which box-shaped cells with a given length are repeatedly connected vertically to one another, needle-shaped discharge electrodes inserted into the box-shaped cells, respectively, a second electrode plate for locating the needle-shaped discharge electrodes thereon, and an insertable and drawable box-shaped case open on top and underside thereof and coupled to the first electrode plate and the second electrode plate therein;
a modular type dust collection device disposed in the flow path of the body, separately from the modular type box-shaped cell type discharge device, to collect the killed viruses and dust passing through the modular type box-shaped cell type discharge device, and having a discharge part with a linear discharge electrode for charging the killed viruses and dust passing through the modular type box-shaped cell type discharge device, a dust collection part for collecting the dust charged through the discharge part, and an insertable and drawable box-shaped case open on top and underside thereof and coupled to the discharge part and the dust collection part therein;
an ozone removal device disposed in the flow path of the body to remove ozone generated from the modular type box-shaped cell type discharge device and/or the modular type dust collection device; and
an air fan disposed in the flow path of the body.

2. The air purifier according to claim 1, wherein the modular type box-shaped cell type discharge device and/or the modular type dust collection device are (is) insertable into and drawable from the body.

3. The air purifier according to claim 1, wherein the modular type box-shaped cell type discharge device is a streamer discharge device.

4. The air purifier according to claim 1, wherein the insertable and drawable box-shaped case whose top and underside are open is a rectangular case and has plastic insulation members disposed on top and bottom corners thereof so that the modular type box-shaped cell type discharge device slides from the body and is insulated from the body.

5. The air purifier according to claim 4, wherein the modular type box-shaped cell type discharge device has mixing holes formed on wall surfaces of the box-shaped cells to mix the active species between the neighboring box-shaped cells.

6. The air purifier according to claim 5, wherein some of the mixing holes are formed at positions corresponding to the needle-shaped discharge electrodes.

7. The air purifier according to claim 1, wherein the modular type dust collection device comprises: the discharge part with the linear discharge electrode constituted of metal wires disposed side-by-side at given intervals and relative electrode plates disposed between the neighboring metal wires of the linear discharge electrode; and the dust collection part having a plurality of dust collection plates for collecting ionized particles exhausted from the discharge part.

8. The air purifier according to claim 7, wherein the metal wires of the linear discharge electrode are metal wires made by twisting stainless nanowires.

9. The air purifier according to claim 1, wherein the ozone removal device comprises an ozone removal catalytic device and an ozone removal light irradiation device.

10. The air purifier according to claim 9, wherein the ozone removal catalytic device comprises horizontal plates each having box-shaped cells connected to one another in left and right directions and filled with catalytic particles containing manganese dioxide particles.

11. The air purifier according to claim 1, further comprising a negative ion generation device.

12. The air purifier according to claim 1, further comprising a negative ion generation device.

13. The air purifier according to claim 3, wherein the insertable and drawable box-shaped case whose top and underside are open is a rectangular case and has plastic insulation members disposed on top and bottom corners thereof so that the modular type box-shaped cell type discharge device slides from the body and is insulated from the body.

* * * * *